United States Patent
Shenderova et al.

(10) Patent No.: US 9,283,155 B1
(45) Date of Patent: *Mar. 15, 2016

(54) NANODIAMOND UV PROTECTANT FORMULATIONS

(71) Applicant: INTERNATIONAL TECHNOLOGY CENTER, Research Triangle Park, NC (US)

(72) Inventors: Olga A. Shenderova, Raleigh, NC (US); Varvara P. Grichko, Sun Valley, CA (US)

(73) Assignee: International Technology Center, Raleigh, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/273,759

(22) Filed: May 9, 2014

Related U.S. Application Data

(63) Continuation of application No. 11/991,090, filed as application No. PCT/US2006/033627 on Aug. 25, 2006, now Pat. No. 8,753,614.

(60) Provisional application No. 60/712,507, filed on Aug. 30, 2005.

(51) Int. Cl.

| | |
|---|---|
| *A61K 8/00* | (2006.01) |
| *A61K 8/29* | (2006.01) |
| *A61K 8/31* | (2006.01) |
| *A61K 9/14* | (2006.01) |
| *A61K 8/19* | (2006.01) |
| *A61Q 17/04* | (2006.01) |
| *A61K 8/04* | (2006.01) |
| *A61K 8/30* | (2006.01) |

(52) U.S. Cl.
CPC ... *A61K 8/19* (2013.01); *A61K 8/04* (2013.01); *A61K 8/30* (2013.01); *A61Q 17/04* (2013.01)

(58) Field of Classification Search
CPC .. C09D 7/1258; C09D 7/1268; C04B 14/022; C04B 3/04
See application file for complete search history.

(56) References Cited

U.S. PATENT DOCUMENTS

| | | | |
|---|---|---|---|
| 6,159,453 A | 12/2000 | Avnir | |
| 6,187,298 B1 | 2/2001 | Kurz | |
| 7,294,340 B2 | 11/2007 | Sung | |
| 8,168,413 B2 | 5/2012 | Chang | |
| 8,574,536 B2 | 11/2013 | Boudou | |
| 2004/0228813 A1 | 11/2004 | Candau | |
| 2008/0118966 A1 | 5/2008 | Chang | |
| 2010/0135890 A1 | 6/2010 | Boudou | |

FOREIGN PATENT DOCUMENTS

| | | |
|---|---|---|
| AU | 2002-344443 A1 | 5/2004 |
| JP | 04295416 A | 10/1992 |
| JP | 2003-081768 A1 | 3/2003 |
| WO | 2004029246 A1 | 4/2004 |
| WO | 2004/039346 A1 | 5/2004 |

OTHER PUBLICATIONS

Higuchi et al. "Cosmetics", Mar. 19, 2013, Translation of JP 2003081768.
Horino, "Cosmetics", Oct. 20, 1992, Abstract of JP 04395416 A.
ISR for Application PCT/US2006/033627, Filed Aug. 25, 2006.
Written Opinion OFISA; Application No. PCT/US2006/033627; Filed Aug. 25, 2006.
Fox; "Patterned Diamond Particle Films"; Journal of Applied Physics; vol. 87, No. 11; Jun. 2000.
Morfesis; "Physiochemical Characterization of Nanosize Zinc Oxide and Titanium Dioxide Used As UVR Sunscreen Agents in Cosmetic Formulations"; NTSI Nanotech 2005.
Casey; Expoloring the Structure-Function Relationship in Multifunctional Nanoparticles; NTSI—Nanotech 2005.
Cayton; "The Impact of Nano-Materials on Coating Technologies"; NTSI—Nanotech 2005.
Justice; Office Action in U.S. Appl. No. 11/991,090; Sep. 23, 2013.
Patel; Office Action in U.S. Appl. No. 11/990,948; Oct. 31, 2012.
Yu; Office Action in U.S. Appl. No. 11/991,090; Jul. 25, 2011.
Patel; Office Action in U.S. Appl. No. 11/990,948; Feb. 13, 2012.
Yu; Office Action in U.S. Appl. No. 11/991,090; Jan. 31, 2012.
Patel; Office Action in U.S. Appl. No. 11/990,948; Aug. 15, 2013.

*Primary Examiner* — Gina Justice
(74) *Attorney, Agent, or Firm* — Jerry A. Miller; Miller Patent Services

(57) ABSTRACT

A dispersion preparation provides transmission attenuation of ultraviolet A and ultraviolet B and ultraviolet C light comprises a dispersion of an effective amount of diamond nanoparticles in a physiologically compatible medium, where the diamond nanoparticles have a size greater than about 60 nm and are modified to enhance absorption of UV radiation. This abstract is not to be considered limiting, since other embodiments may deviate from the features described in this abstract.

40 Claims, 12 Drawing Sheets

_NANODIAMOND UV PROTECTANT FORMULATIONS_

CROSS REFERENCE TO RELATED DOCUMENTS

This application is a continuation of allowed U.S. patent application Ser. No. 11/991,090 filed Apr. 29, 2009 which is a national stage entry of PCT application no. PCT/US06/33627 filed Aug. 25, 2006 which claims priority benefit of Provisional Patent Application No. 60/712,507 filed Aug. 30, 2005 to Shenderova, et al., each of which are hereby incorporated by reference.

COPYRIGHT NOTICE

A portion of the disclosure of this patent document contains material which is subject to copyright protection. The copyright owner has no objection to the facsimile reproduction of the patent document or the patent disclosure, as it appears in the Patent and Trademark Office patent file or records, but otherwise reserves all copyright rights whatsoever.

BACKGROUND

Sunscreen preparations, including cosmetics that contain sunscreens, are used to protect human skin and other tissue from the damaging effects of ultraviolet (UV) rays. Among the more effective and successful sunscreen products are those that utilize Titanium Dioxide ($TiO_2$) and Zinc Oxide (ZnO). Others use organic UV absorbers. Some of the more effective of these formulations are visible in use, while others blend with the skin or otherwise become transparent.

The ultraviolet radiation (UVR) spectrum has two distinct regions that are of concern for human health: UVB (290-320 nm) and UVA (320-400 nm). Both UVA and UVB radiation exposure, from the sun or artificial sources are hazardous. UVB causes sunburn and skin cancer in humans. UVA causes skin damage, reduces skin elasticity and induces wrinkles and also contributes to sunburn and cancer. Also, UVA radiation is a year-round phenomenon. UVA radiation passes through window glass and penetrates deeper into the skin than UVB radiation, while UVB radiation is blocked by window glass. High intensities of UVB light are hazardous to the eyes, and exposure can cause welder's flash (photokeratitis or arc eye) and may lead to cataracts, pterygium, and pinguecula formation. A UV attenuating formulation preferably includes both a UVA and a UVB blocking constituents ("broad spectrum" coverage) to prevent most of the UV radiation within the range of about 290-400 nm from reaching human skin, hair or other organs and tissues. There is also so called UVC radiation within 100-290 nm wavelength range, the strongest and potentially most harmful form. While UVC produced by the sun is almost entirely absorbed by the earth's ozone layer and is therefore not usually considered a health concern below the ozone layer, it should be noted that the UVC radiation can be found in mercury arc lamps, germicidal lamps and other sources.

Currently both organic and inorganic sunscreens are commercially available. To satisfy the "broad spectrum" attenuation criteria in many formulations it is common practice to utilize two or more active ingredients with complimentary absorbance spectra since typical organic or inorganic sunscreens block only a portion of the total UVR spectra. When organic sunscreen preparations are used, issues of photo-induced and non-photo induced toxicity and allergy have been observed due to long-term use of organic sunscreens and are becoming increasingly of concern.

Among the organic UV radiation absorbing ingredients of UVB filters that are used in commercial sunscreen formulations in the U.S.A. are paramethoxycinnamic acid esters, such as 2-ethylhexyl paramethoxycinnamate, commonly referred to as octyl methoxycinnamate or PARSOL MCX, octyl salicylate, and oxybenzone. The common organic UVA filters used in commercial sunscreen formulations are the dibenzoylmethane derivatives, particularly 4(1,1-dimethyl-ethyl)-4'-methoxydibenzoylmethane, which is also called avobenzone and sold under the name PARSOL 1789. Other dibenzoylmethane derivatives and other organic compounds can also be used as UVA filters.

The above described UVA filters can rapidly degrade, when used alone or when combined with the UVB filters. Typically, the UVB filters are combined with the UVA filters in an oil-based formulation. This oil solution or "oil phase", as it referred to by formulators of cosmetic products and sunscreens, is then mixed with an aqueous solution to make an emulsion, which becomes the cream or lotion form of a sunscreen or cosmetic. There can be a situation when one photoactive compound in a sunscreen formulation promotes photodegradation of another photoactive compound in the composition. For example, when avobenzone is combined with octyl methoxycinnamate, rapid photodegradation of both the dibenzoylmethane derivative and the octyl methoxycinnamate is observed.

The most common inorganic sunscreen agents include ZnO and $TiO_2$ particles. They can be suspended either in oil or water based media, as opposed to organic sunscreens agents that are mostly soluble in oil-based media used in cosmetic formulations. By appearance, both ZnO and $TiO_2$ are white pigments with $TiO_2$ demonstrating more visible "whiteness" than ZnO. The degree of perceived transparency depends on many factors including how much of sunscreen formulation is applied to the skin ("thickness") and the concentration of the particles in the formulation. In formulations with high SPF factors, these agents are quite visible on the skin, which may be undesirable for some users and for use over large areas of the body.

When used in combination, ZnO and $TiO_2$ are generally considered complimentary and provide higher degrees of UVA and UVB protection than when used alone. However, preparation of the mixtures of these particulates requires special processing (for example, separate dispersion of the ZnO in the oil phase and the TiO2 initially in the water phase. There is also currently a concern that when ZnO and $TiO_2$ are formulated with smaller particle sizes, the rate at which harmful hydroxyl radical generation increases due to the inherent photoactivity of these materials.

UV radiation can also degrade cosmetic formulations and cosmetic products, such as, for example, the structural component such as the polymer as well as the color agents such as pigments or dyes. This photo-induced degradation can lead to color fading and deterioration effects which are undesirable in the cosmetic product.

BRIEF DESCRIPTION OF THE DRAWINGS

Certain illustrative embodiments showing organization and method of operation, together with objects and advantages may be best understood by reference detailed description that follows taken in conjunction with the accompanying drawings in which.

DETAILED DESCRIPTION

Figure 1:
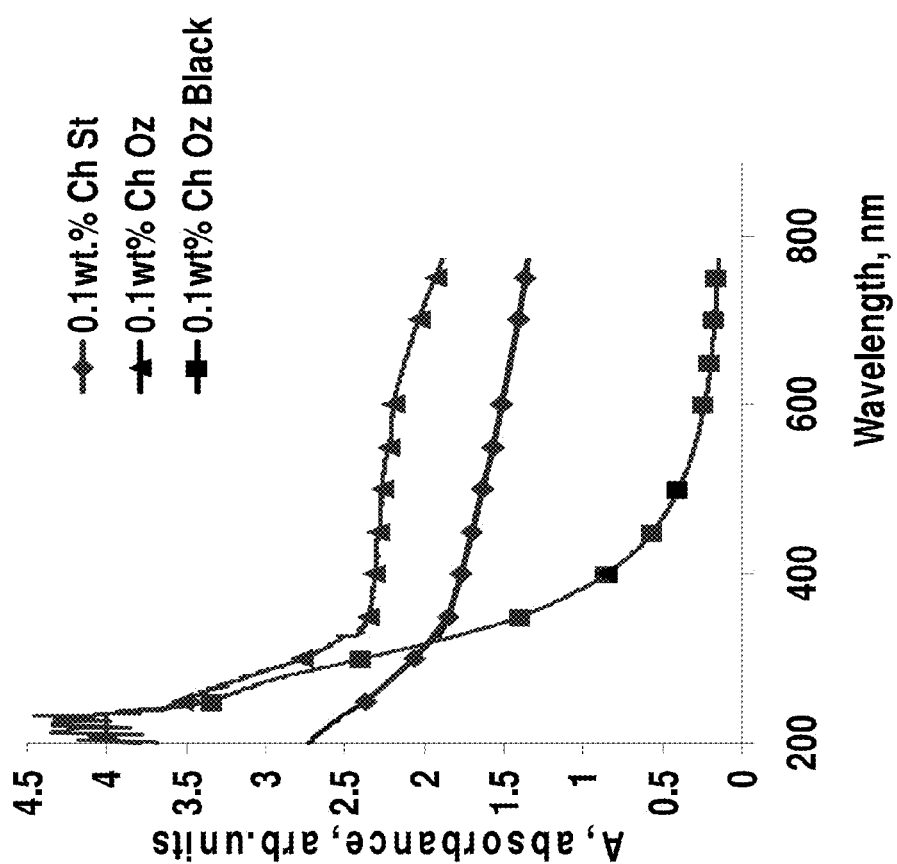
FIG. 1 illustrates UV-VIS (ultraviolet through visible) absorbance spectra of 0.1 wt % of two types of nanodiamond particles (Ch St and Ch Oz) dispersed in deionized water (DI) water. Polydispersed Ch Oz and one of the fractions of Ch Oz nanodiamond (Ch Oz Black) are used in the analysis.

While this invention is susceptible of embodiment in many different forms, there is shown in the drawings and will herein be described in detail specific embodiments, with the understanding that the present disclosure of such embodiments is to be considered as an example of the principles and not intended to limit the invention to the specific embodiments shown and described. In the description below, like reference numerals are used to describe the same, similar or corresponding parts in the several views of the drawings.

The terms "a" or "an", as used herein, are defined as one or more than one. The term "plurality", as used herein, is defined as two or more than two. The term "another", as used herein, is defined as at least a second or more. The terms "including" and/or "having", as used herein, are defined as comprising (i.e., open language).

Reference throughout this document to "one embodiment", "certain embodiments", "an embodiment" or similar terms means that a particular feature, structure, or characteristic described in connection with the embodiment is included in at least one embodiment of the present invention. Thus, the appearances of such phrases or in various places throughout this specification are not necessarily all referring to the same embodiment. Furthermore, the particular features, structures, or characteristics may be combined in any suitable manner in one or more embodiments without limitation.

The term "or" as used herein is to be interpreted as an inclusive or meaning any one or any combination. Therefore, "A, B or C" means "any of the following: A; B; C; A and B; A and C; B and C; A, B and C". An exception to this definition will occur only when a combination of elements, functions, steps or acts are in some way inherently mutually exclusive.

For purposes of this document, the prefix "nano" as used, for example in "nanoparticle" is intended to refer to particles having length in at least one dimension in the range of approximately 1-1000 nanometers. However, in some particular cases, the length scale for achieving the novel properties and phenomena consistent with certain embodiments of the present invention may be less than 1 nanometer or be slightly larger than 1000 nanometers.

For purposes of this document, the terms UV absorbers, filters, sun blocks, UV protectants, sunscreens, UV attenuation, and the like will generally be used interchangeably without regard for any particular mechanism that causes the material to behave to protect against ultraviolet radiation, except in the context of a particular theorized mechanism that provides the exhibited characteristics. It will be recognized by those skilled in the art that various mechanisms may operate in such products to produce the desired effect including reflection, dispersion, scattering, photoreactions and absorption. Any presentation of theory of the UV protection mechanism is presented to explain the Applicants' current understanding of the operational mechanism and is not to be considered limiting in any way, since at this writing such information may only constitute unproven theory.

Embodiments consistent with the present invention utilize nanoparticles of diamond. In order to understand this discussion, it is important to have an understanding of the accepted terminology that will be used herein when discussing particle size. The term "primary particle size" (PPS) is the size of a smallest primary structure in a system. This size distribution is typically rather narrow and depends on the particle synthesis conditions. Most suppliers of nanoparticles list only primary particle size in their product specification. This particle size is typically defined from x-ray diffraction pattern, Scanning-Electron Microscopy (SEM), High-Resolution Transmission-Electron Microscopy (HRTEM) images or calculated from Brunauer, Emmett and Teller (BET) surface area measurements. However, the primary particles can form aggregates or agglomerates due to their high surface energy or fabrication/processing conditions. The size of the aggregates is referred to as the "aggregate" or "agglomerate" size herein to clearly call out the distinction. The term "particle size" (PS) is used to generically refer to either PPS or agglomerate size or a size of a combination of agglomerates and primary particles.

Agglomerate size can be measured in a number of ways (e.g., SEM for dry powder forms or unimodal analysis of photon correlation spectroscopy data for relatively transparent solutions) and often can be tens or hundreds of times bigger than the PPS. In this document, the term "particle size", as defined above, can refer to either primary particle size or the agglomerate size or a combination of primary particles and agglomerates. For clarity "primary particle size" or "agglomerate size", will be explicitly called out when appropriate. The term nanodiamond or diamond nanoparticles is used for submicron sized particles and may include both or either primary particles and particles formed by agglomerates of the primary particles.

For purposes of this discussion, particle size and agglomerate size was measured in a variety of ways including using unimodal analysis of photon correlation spectroscopy (in this case, by setting the spectroscope to provide output in the unimodal mode) for dispersions in clear liquids. This measurement technique is rapid and has been found to yield consistent measurements compared to other techniques, and thus, measurements presented herein are based upon such measurement when relatively transparent liquids are analyzed, but other standard measurement techniques (e.g., SEM, HRTEM, and BET) will yield similar results and can also be used when such techniques are more suitable.

In accordance with certain embodiments consistent with the present invention, nanodiamond (ND) particle are used to absorb, scatter, reflect or otherwise inhibit the transmission of ultraviolet (UV) transmission to and absorption by human tissue (e.g., skin, hair, eye, mucus membrane, etc.). While all aspects of the mechanism for the absorption of UV by nanodiamond particle agglomerates may not currently be fully understood, throughout this document various theoretical aspects of this action are interjected in order to better teach the various embodiments of the invention as currently understood. However, it is to be fully understood that such discussions of the theory as to why ND particle agglomerates behave in this manner is not to be considered limiting on embodiments of the present invention. That is, the claimed inventions are not bound by any theory presented herein, and disclosures of theory should be considered just that—theory.

Nanodiamond UV absorption spectra depend on a number of physical and chemical properties of the ND particles such as particle size, physical state, impurities, surface chemical group and their concentration. ND particles can be modified as a result of wet or gas phase chemical reaction(s), or chemical reactions induced photo-chemically, electrochemically, mechanochemically, or by means of a plasma, or sonic energy or other means to obtain ND particles with an enhanced ability to absorb UV radiation.

In certain embodiments consistent with the invention, compounds and methods are provided to develop a new class of UV sunscreen compositions. In other embodiments, particular sunscreen compositions are provided. More particularly, diamond nanoparticle agglomerates are used to formulate sunscreen and UV protective compositions such as cosmetics.

Use of diamond particles in UV sunscreening formulations can be very beneficial. Bulk diamond has a refractive index of approximately 2.4. Thus diamond particles scatter light very efficiently. Such diamond particles have been discovered to be strong absorbers of UVB and UVA radiation, as well as UVC radiation. Thus, diamond nanoparticles provide a single physical absorber of both UVA and UVB radiation to avoid the complications connected with processing of a sunscreen formulation when combining different type of particles or organic actives (which does not preclude use of such additives to further enhance the UV protective qualities of a given formulation).

While a complete understanding of the strong absorption in UV spectra of radiation by nanodiamond particles is yet to be revealed, possible mechanisms theorized for causing the absorption include absorption by the atoms with $sp^2$ bonding terminating a part of the particles surfaces; the surface groups involving other elements in addition to carbon; photoluminescence caused by internal defects in the bulk of diamond particles and other phenomena. For example, there are several defect centers due to dopant atoms (N, B and other elements), self-interstitials, vacancies, complexes of the above, complexes of the charged defects, dislocations that cause absorption and photoluminescence, particularly at wavelengths shorter than 420 nm. That means that UV light is absorbed by these structural features and then is reemitted at a longer wavelength, primarily in visible range of light for the case of photoluminescence.

While the fundamental absorption edge of bulk diamond is at a wavelength of about 220 nm (the band-gap of diamond is 5.5 eV), there are reports on effective band gaps in ultradispersed diamond particles within the range of ~3 eV. Dopants, surface states, internal defects and atomically sharp grain boundaries observed between primary diamond particles are all believed to contribute to the formation of the sub-bands within a fundamental band gap and thus cause the UV absorption at wavelengths longer than those corresponding to the fundamental band-gap.

The photoluminescence and other types of absorption of UV radiation in diamond particles are believed to be possibly due to defects that are present naturally as a result of material formation/processing or created by subsequent irradiation (for example, electron, proton, high energy ions, alpha or gamma-radiation or other types of irradiation) or obtained by subsequent annealing or created by other means. In accordance with certain embodiments, diamond particles that actively absorb UVB and UVA radiation can be used in UV sunscreen formulations and cosmetics with sunscreen attributes alone or in combination with other UV filters.

There are also other benefits of using diamond particles as UV filters. Diamond particles possess a chemically inert core that provides additional benefits for its use in sunscreen formulations. Use may be made of diamond particulate because it is non-toxic and biocompatible. UV light that is still getting through sunscreens generates free radicals that can damage skin. Since diamond nanoparticles are reported to scavenge free radicals a further benefit may be obtained in protecting human skin and sunscreen or cosmetic compositions from being damaged or bleached as a result of UV-induced radical chain reactions. The surface of the diamond particles can be easily functionalized with a very broad variety of different functional groups that can facilitate dispersion of diamond particles in different compositions.

As will be described with reference to various publications below, which are hereby incorporated by reference, diamond nanoparticles can be produced by several means, and which will result in varying primary particle sizes and varying agglomeration characteristics (see O. Shenderova and G. McGuire, Types of Nanodiamonds, book chapter in "Ultrananocrystalline diamond: Synthesis, Properties and Applications", Editors: O. Shenderova, D. Gruen, William-Andrew Publisher, 2006). Isolated nanocrystalline diamond particles with characteristic sizes of several tens of nanometers can be monocrystalline or polycrystalline. Monocrystalline particles are obtained by processing of micron-sized diamond particles, which are, in turn, a byproduct of natural diamond or HPHT diamond synthesis. Synthetic diamond particles with sizes below ~50 microns represent the raw material for making micron and sub-micron diamond size particles.

The processing of micron sized diamond particles to smaller fractions includes micronizing, purification and grading of the powder. The polycrystalline nanodiamond powder can be processed from micron sized polycrystalline diamond particles obtained by shock wave synthesis. Under suitable conditions, explosively produced shock waves can create high pressure-high temperature conditions in confined volumes for a sufficient duration to achieve partial conversion of graphite into nanometer-sized diamond grains (~20 nm) which compact into micron-sized, polycrystalline particles. The processing of micron sized diamond particles to smaller fractions includes micronizing, purification and grading of the powder. For example, range of polycrystalline or monocrystalline nanodiamond particles described above which are sold by Microdiamant AG, Switzerland Range include smallest fraction sizes 0-50 nm (median size: ~25 nm), 0-100 nm (median size 50 nm), 0-150 nm (median size 75 nm) and larger fractions for polycrystalline diamond and 0-250 nm (average size 125 nm) fraction and larger size fractions for monocrystalline natural diamond particles. Currently, Frenklach and co-workers [Frenklach M, Kematick R Huang D, et. al., Homogeneous nucleation of diamond powder in the gas phase, *J. Appl. Phys* 66, 395-399, 1989] studied nucleation and growth of nanodiamond powder directly in the vapor phase in a substrate-free low-pressure microwave-plasma chemical vapor deposition (CVD) reactor. The particles were collected downstream of the reaction zone on a filter within the tubular flow reactor and subjected to wet oxidation to remove non-diamond carbon. The homogeneous diamond nucleation took place when a dichloromethane- and trichloroethylene-oxygen mixture were used as source material. The particles had crystalline shapes with an average particle size of around 50 nm. A mixture of diamond polytypes were observed in the powder. Frenklach et al. [Frenklach M., Howard W., Huang D., et al., Induced nucleation of diamond powder. Appl. Phys. Lett., 59, 546, 1991.] also studied the effects of heteroatom addition on the nucleation of solid carbon in a low-pressure plasma reactor. The addition of diborane ($B_2H_6$) resulted in substantial production of diamond particles, 5 to 450 nm in diameter, under the same conditions that show no diamond formation without the presence of diborane. Recently, spherical, rather monodispersed diamond particles with diameters of different fractions in the range from 150 to 600 nm have been synthesized in a gas phase by multi-cathode direct current plasma activated CVD [Lee J K, Baik Y J, Eun K Y, et al., Synthesis of diamond spheres Chem. Vap. Depos., 10, 133, 2004]. The internal structure of a spherical particle consist of nanocrystalline diamond grains ~30 nm in size. Other methods of nanodiamond formation include ion irradiation of graphite, chlorination of carbides, and several other possible methods to produce such diamond particles.

One of the most popular commercial nanodiamond products is nanodiamond produced by detonation of carbon-containing explosives (the primary particle size produced by this method is approximately 3-5 nm in most currently popular commercial products, although monocrystallite particle sizes up to 50 nm can be also observed). Primary nanodiamond particles produced by detonation of carbon containing explosives form both tightly bonded aggregates (possibly fused during the detonation process) and loosely bonded aggregates. Recently, using stirred-media milling technique, it was shown possible to de-agglomerate detonation nanodiamond down to their primary particle sizes, 4-5 nm. The slurries of 4-5 nm detonation nanodiamond particles can be resistant to agglomeration for a long period of time [A. Kruger, F. Kataoka, M. Ozawa, et al., Unusually tight aggregation in detonation nanodiamond: identification and disintegration, Carbon 43 (8), 1722-1730, 2005]. As was mentioned above, different means of enhancement of UV absorption by different types of nanodiamond particles can be achieved. The above documents are hereby incorporated by reference herein.

The experimental examples presented herein generally used agglomerates of detonation diamond nanoparticles, and the sizes presented are generally sizes of such nanoparticles. However, as noted above, primary particles of similar sizes are expected to perform in a similar manner. Hence, the present invention is not limited to agglomerates of smaller primary particles, but also encompasses use of larger primary particles than those of the DND used in the experiments.

Commercially obtained nanodiamond powder produced by a detonation process, detonation nanodiamond (DND), is a polydispersed powder of particles mostly within the 10-1000 nm size range. These polydispersed nanodiamond particles can be fractionated into fractions with small and large particles with relatively narrow particle size distributions, with the size represented herein being measured using unimodal analysis of photon correlation spectroscopy data. These are the sizes of nanodiamond fractionated particles, largely aggregates, that are used throughout this discussion unless otherwise designated. The sizes are measured by the photon correlation spectroscopy method when particles are dispersed in a liquid media or otherwise measured using SEM. The particle sizes referenced are thus a type of average values (assuming spherical shapes) of irregular shaped aggregate particles of diamond, as is conventional in this field. Examples of available nanodiamond fractionated particles include particles with 25 nm, 35 nm, 50 nm, 60 nm, 70-80 nm, 100 nm, 150 nm and larger particle sizes. Examples of fractionation approaches include ultracentrifugation.

Based upon experiments conducted to date, there appears to be several advantages of using detonation nanodiamonds as UV filters (but this does not imply that nanodiamond produced by other means cannot be used). These particles demonstrate strong luminescence when excited by UV radiation, probably due to numerous internal defects formed during particle synthesis (nitrogen-related defects for example, since nitrogen is a constituent of the explosives used for the synthesis). Strong UV absorption can be also possibly attributed to the $sp^2$ termination of a part of a particle surface formed during subsequent particle processing. The particles contain a wide variety of surface groups such as carboxyl, hydroxyl, amino, carbonyl and other groups some of which may contribute to the absorption. Additionally it is noted that detonation nanodiamonds are intrinsically hydrophilic, thus they can form stable hydrosols. At the same time, some of them can be dispersed in a variety of alcohols and oils (for example, nanodiamond purified with ozone) even without additional surface modification. Surface modification methods are also well developed for nanodiamonds to be dispersed in polar and non-polar media. For example, heat treatment of ND in air atmosphere at temperature 350-450° C. within an hour improves its dispersivity in water; surface fluorination in atmospheric plasma system using fluorine-containing gases helps improve dispersivity in acetone, alcohols and some oils. Dispersion of nanodiamonds in different media can be done using ultrasonic energy, shaking, magnetic stirring and other methods. Reduction of sizes of nanodiamond aggregates can be done by grinding, milling, treatment in atmospheric or sub-atmospheric pressure plasma and by other methods.

According to certain embodiments consistent with the present invention, a diamond particulate composition has UV attenuating diamond particles with an agglomerate size greater than about 60 nm and generally less than about 1 micron. The composition can optionally further incorporate a composition of such particles in combination with other sunscreen agents that can be chosen from organic screening agents, inorganic physical screening agents and their mixtures. The composition can comprise a chemical sunscreen agent or any UVA and/or UVB and/or UVC screening agent, which can be used in the cosmetics field by appropriate dispersion in a physiologically acceptable carrier (i.e., cosmetically or dermatologically acceptable medium) such as a lotion, cream, powder, oil, gel, wax, emulsion, solvent or other cosmetic base. The term "physiologically" compatible or acceptable medium, agent, vehicle or carrier is understood to mean a medium suitable for topical application to human or animal skin, lips, hair, mucus membrane, eyes or other organs and tissues. These terms can be used interchangeably herein with cosmetically acceptable or cosmetically compatible or dermatologically acceptable or compatible.

A wide variety of base materials and additives can be used in conjunction with formulation of cosmetic and sunscreen products including many of those included in the current Cosmetic, Toiletry and Fragrance Association (CTFA) Cosmetic Ingredient Dictionary and Handbook, $11^{th}$ edition, 2006, which is incorporated herein by reference and describes a wide variety of cosmetic and pharmaceutical ingredients commonly used in skin care compositions, which are suitable for use in the compositions of the present invention. Such ingredients, include but not limited to lotions, creams, moisturizers, absorbents, abrasives, anticaking agents, antifoaming agents, antioxidants, binders, biological additives, buffering agents, bulking agents, chelating agents, chemical additives, colorants, cosmetic astringents, cosmetic biocides, denaturants, drug astringents, external analgesics, film formers, fragrance components, pH adjusters, plasticizers, preservatives, propellants, reducing agents, skin bleaching agents, skin-conditioning agents (emollient, humectants, miscellaneous, and occlusive), skin protectants, solvents, foam boosters, hydrotropes, solubilizing agents, suspending agents (nonsurfactant), other sunscreen agents and ultraviolet light absorbers, waterproofing agents, viscosity increasing agents (aqueous and nonaqueous), emollients, humectants, dry-feel modifiers, waterproofing agents, insect repellants, preservatives, sunless artificial tanning agents, antioxidants, vitamins chelating agents, fragrances, pH modifiers and other ingredients that are used in cosmetic formulations for topical application to human tissue. It is contemplated that most such materials will be compatible with ND formulations as taught herein.

Often, cosmetically acceptable and aesthetically pleasing skin products are preferably visually transparent or nearly so (but, note that embodiments consistent with the present invention are not necessarily visually transparent). The same is true for selected hair spray and other cosmetics. Detonation diamond particles with size less than approximately 120-150 nm in diameter can provide the advantage of forming highly uniform nanofine dispersions with a high translucency factor (at concentrations, for example in water ~0.1 mass %). In addition, nanodiamond particles might provide the advantage of requiring a smaller amount of particulate per unit of surface as compared to other UV attenuating materials to be protected from UV light to achieve the desired SPF.

According to certain embodiments, sunscreens and cosmetics can be formulated to contain as-purified diamond particles, functionalized diamond particles or diamond particles with attached organic molecules that are made particularly suitable for use with the desirable carrier, agent or solvent (liquid, solid or aerosol, and etc.). The vehicle may be an aqueous solution, or a polar organic solvent, alcohol, e.g. ethanol or other polar-solvent; natural or synthetic oil; an oil-in-water emulsion; or a water-in-oil emulsion; or a wax; and the like.

In accordance with certain embodiments consistent with the present invention, nanodiamond-derived primary particles and agglomerates can be used as a UV absorber, sunscreen and photostabilizer, including nanodiamonds produced by detonation, shock wave, chemical vapor deposition (CVD), high-pressure-high-temperature (HPHT), and other methods as noted above and yet to be developed methods. Such agglomerates can be, in addition, doped or modified chemically (wet chemistry, gas phase reactions, catalytic conversion), electrochemically, mechanochemically, sonochemically, photochemically, by exposure to radiation and beams, by oxidation, for example, with acids, oxygen or ozone, or with plasma treatment and other methods to enhance absorption of UV radiation by creating of structural defects, $sp^2$ bonded surface termination and surface functional groups attached to the ND surface by either covalent or non-covalent bonds. It is also possible to perform functionalization of diamond particulate in a gas plasma discharge.

Also, diamond particles can be modified to enhance the stability of their dispersions in a suitable carrier or liquid, provide chemical compatibility and assure surface adhesion of cosmetic preparations. In addition, diamond and other carbon-based particulate may form complexes with organic molecules to enhance UV light absorption.

The energy of the UV radiation absorbed by diamond particles may be converted into energy of chemical bonds, scattered, dissipated as heat or converted into energy of photoluminescence. The diamond nanoparticles actively scatter light as a function of condition, particle size and shape, wavelength, polarization state, and angle of incidence. This is expected to reduce the amount of absorbed energy converted to heat and may provide additional aesthetic effect by either contributing to the color or other visible characteristics of cosmetic formulations including foundations, concealers, lip glosses and lipsticks or other cosmetic formulations.

According to certain embodiments consistent with the present invention, a formulation of cosmetic product with aesthetic appeal has diamond particles exhibiting photoluminescence under UV or other light due to the presence of N—V centers or other structural features. In the composition according to this embodiment, desired photoluminescent diamond particles that contain different color centers are added to cosmetic products such as under eye concealer, other concealers, lip gloss, hair spray or other cosmetic formulations. The emitted light wavelength is determined by the intrinsic diamond particle properties, excitation light and properties of the formulation.

According to certain embodiments of the present invention, the formulation of cosmetic products can be augmented with diamond particles of a chosen color e.g., white, violet, brick or other colors alone or in combination with other coloring agents. Doping of ND to induce colored centers can be realized by several means including at the stage of detonation of the explosives used to produce the ND by the addition of materials to the explosives that induce color variations. Doping can be also induced by radiation and other means known in the art.

Experiments have been conducted with quantities of ND particles as low as 0.01 wt. % which have realized substantial ultraviolet absorption. In commercial formulations for sunscreen or cosmetic applications, an addition of perhaps as low as 0.1 wt. % or 0.5 wt. % or even lower may provide beneficial enhancement to sunscreen and similar products for enhancement of UV protection. Further, addition of 1-2 wt. % or greater, perhaps as much as 3 wt. % to 5 wt. % could provide even higher benefits in protection against UV. In some applications as high as 10 wt. % or even higher is projected to be useful for providing high degrees of UV protection, although high concentrations may contribute to visibility of the ND particles. Of course, the appropriate concentration of ND or similar materials can be determined experimentally according to the base material and the desired effect. Systematic trials of varying percentages of ND blended uniformly as an admixture with the desired base material can be done to determine the amount needed to achieve the desired result for any given base material. Thus, the above ranges should be considered as a starting point for straightforward experimental determination of the concentration needed to achieve a desired result.

Figure 12:
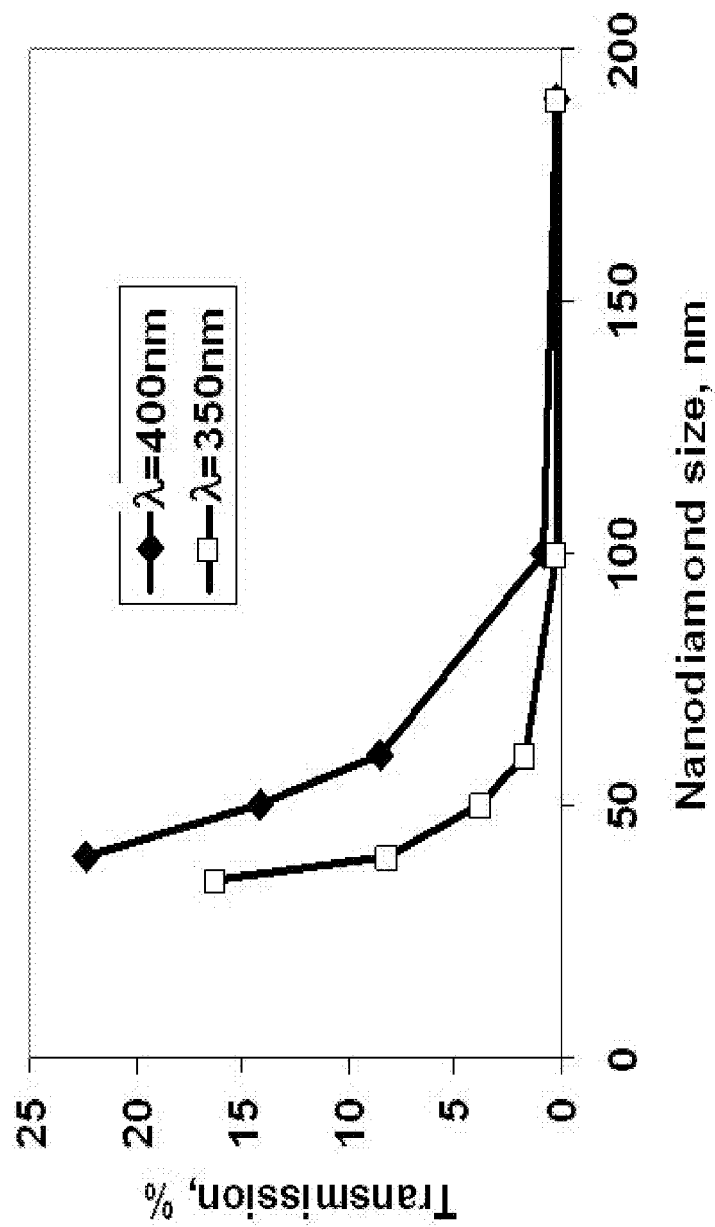
FIG. 12 illustrates light transmission as a function of agglomerate size at two particular wavelengths from the UV spectrum.

As will be seen in the experimental data, there is a surprisingly strong change in the absorption of UV rays in the longer UV wavelengths that is dependent upon the nanodiamond particle size. This dependency is non-linear and heretofore unreported. At lower particle sizes, the ultraviolet light absorption properties, particularly around 400 nm wavelength, may go unnoticed, but as particle size increases above about 60 nm, the amount of UV absorption is observed to dramatically and surprisingly increase at the upper end of the UV wavelength spectrum by a large factor that appears to have an approximately exponential shape. Under laboratory test conditions, transmission of UV light at 350 nm wavelength has been found to decrease by a factor of about 19 when the size of particles is doubled from 50 nm to 100 nm (3.8% vs. 0.2% of transmitted radiation) as shown in FIG. 12. Transmission of UV light at 400 nm wavelength has been found to decrease by a factor of 15.8 when the size of particle agglomerates is doubled from 50 nm to 100 nm (14.2% vs. 0.9%). Between 60 nm and 100 nm, the light transmission at 350 nm wavelength, transmission was decrease by a factor of 8.5 (1.7% vs. 0.2%), and at 400 nm wavelength, transmission was cut by a factor of 10 (9% vs. 0.9%)

As particle sizes increase to the range of 125 to 150 nm and beyond, the transmission of UV light is extremely highly attenuated across the UV spectrum, but the particle size is such that the formulation may become more readily visible in higher concentrations and application thicknesses. Hence, preferred ranges of particle agglomerate sizes range from about 60 to about 150 nm, with a more preferred agglomerate size range from about 75 to about 125 nm, and about 100 nm being most preferred in formulations where transparency of the particles is desirable. In other embodiments consistent with the present invention, higher concentrations and larger particle sizes can be used when transparency is not an important consideration. Particle agglomerate sizes of approximately 100 nm provide extremely good UV absorption while remaining transparent at relatively high concentrations, and is therefore considered approximately optimum for transparent formulations.

In view of the above noted properties of ND, it appears that these materials can be used not only as efficient UV radiation absorbers, but also visible radiation absorbers. To enhance the ability of ND to absorb UV radiation ND can be combined with an appropriate carrier or other material. Examples of the carriers and materials include, but are not limited to, virtually any base medium used in known sunscreens and cosmetics. The precise quantity of ND to be used in such formulations can be readily determined experimentally based on the desired UV absorbing properties of the final product and its cost, and the effect of ND on color and/or cosmetic clarity of the formulation. Based on the absorption spectra it can be seen that formulations that contain as little as 1% mass with a size of ND particles added to the dispersion of about 60-100 nm shows very substantial beneficial UV absorption and 1.5 mg/cm$^2$ can provide UV absorption comparable to the UV absorption measured for commercially available sunscreens with SPF30.

The ranges of values for the addition of ND particles given herein are to be considered as representative amounts provided as guidance to further refinement and experimentation and should not be considered absolutes or limiting. Additionally, the ranges listed herein are to be interpreted as including every possible smaller range within each range, and when minimum or maximum values are provided, they are intended to be effectively unbound at the opposite end of the range. It is additionally noted that the mechanism and medium used to create the dispersion can result in additional agglomeration into larger particles agglomerates and this should be taken into consideration when developing a formulation since both UV absorption and transparency or translucency will be affected.

EXAMPLES

In the examples described below, nanodiamonds (ND) produced by explosives detonation are used to illustrate the usefulness of nanodiamond in applications for protection from UV radiation. Detonation nanodiamonds (DND) are synthesized at the high pressure-high temperature conditions achieved within the shock wave resulting from the detonation of carbon-containing explosives with a negative oxygen balance. In this method, diamond clusters are formed from carbon atoms contained within explosive molecules themselves, so only the explosive material is used as a precursor material. A wide variety of explosive materials can be used. One example of a typical explosive is a mixture of TNT (2-methyl-1,3,5-trinitrobenzene) and hexogen (hexahydro-1,3,5-trinitro-1,3,5-triazine) (RDX) composed of C, N, O and H with a negative oxygen balance (i.e. with the oxygen content lower than the stoichiometric value required to react with the carbon of the explosive), so that 'excess' carbon is present in the system.

The explosion takes place in an inert (non-oxidizing) to carbon gas medium that plays the role of a coolant and is either gas ($N_2$, $CO_2$, Ar or other medium under pressure) or ice (water), so called 'dry' or 'wet' synthesis, correspondingly. The product obtained by detonation, called detonation soot, contains the diamond nano-particles along with other carbon structures. A variety of techniques can be used to separate the ND phase from soot, for example, by oxidizing the non-diamond carbon. A typical primary particle size of DND is within the size range of 3-5 nm. In the final product, DND powder, nano-diamond primary nano-particles form tightly and loosely bonded aggregates ranging in the largest dimension from several tens to several hundreds of nanometers and up to micrometers. Since as-received powders contain a wide variety of particle sizes, they are called polydispersed. Polydispersed powder can be separated into fractions with narrower particle sizes by known methods (for example, by centrifugation and other methods as described in the above references).

In the examples presented below, several types of DND obtained from different vendors were used for experiments. Some DND were produced in a chamber containing a gas medium as the coolant (Dol, Kr-b) and some types of DND were produced using an ice coating around the detonation charge (Ch St, Ch Oz). Sample Dol was purchased from the Diamond Center, Saint-Petersburg, Russia where it was synthesized by explosion of TNT/RDX in a $CO_2$ atmosphere and oxidized by thermal oxidation (~240-260° C.) using dilute nitric acid under pressure, washed with water, and dried.

Sample Kr-b was purchased from the Institute of Biophysics, Krasnoyarsk, Russia and was produced at Krasnoyarsk Research Center, Russia by explosion of TNT/RDX in a $CO_2$ atmosphere and acid-oxidized, washed with water, and dried. Then the sample was modified by a vendor. Modification is based on incorporation of Na⁺ ions into ND surface. This modification significantly increases the DND dispersivity and hydrosol stability.

Ch St and Ch Oz samples were synthesized from a mixture of TNT/RDX (40/60 wt %) explosives using ice cooling media (purchased from "New Technologies", Chelyabinsk, Russia). Ch St ND was obtained by the detonation soot purification process using a mixture of sulfuric acid with chromic anhydride treatment, washed with water, and dried. Ch Oz ND was purified from the soot in an ozone-flow reactor ('dry' oxidation method). The size of the primary particles for both samples was about 4 nm. Further modification of the Ch St sample was performed at the vendor site. Sample Ch St was additionally purified using ion-exchange resins, heat treated in an air atmosphere and fractionated by centrifugation down to 150 nm particle size when dispersed in water and measured using PCS. This modified sample is called Ch 16 in the experiments below.

From several DND, samples fractions of smaller particle sizes were produced for selected experiments. First, the initial DND powder was dispersed in DI water using a custom made direct-immersion horn-type ultrasound sonicator with an output power of 100-400 W. Then, the DND hydrosol was centrifuged at 20° C. using a multipurpose refrigerated centrifuge (Thermo Electron Corporation) equipped with a 17.5-cm fixed angle rotor and 50-mL conical centrifuged tubes. Centrifugation time varied between 5 minutes and 50 minutes depending on the fraction size of interest. G-forces varied between 1,000 g and 25,000 g. DND particle size distributions in their hydrosols were measured by photon correlation spectroscopy (PCS) using a Beckman-Coulter N5 submicron particle size analyzer.

The surface chemistry of the samples under investigation is very different due to different methods of purification and modification applied to the samples. TABLE 1 summarizes the content of surface groups of the samples studied using FTIR spectra. FTIR spectra were obtained with a Varian 7000e FTIR spectrometer in transmission mode with averaging over 500 spectra. A wide variety of surface groups is observed for the ND samples under study. The type of surface groups influence dispersivity of DND in different solvents and materials as well as their resistivity to agglomeration and sedimentation. For example, the most stable water and alcohol suspensions can be formed from Ch Oz, Kr-b, and Ch 16. Stable oil-based suspensions can be also formed based on these ND (for example using Ch Oz and Ch 16). Surface groups of the nanodiamonds can be changed by known reactions in order to improve their dispersivity and resistance to agglomeration and sedimentation in different polar and non-polar media.

The graphs below illustrate absorbance (A=∈lC, ∈—extinction coefficient, l—sample thickness C—concentration) as a function of wavelength in nanometers. Absorbance $A = \log_{10}(I_0/I)$, where $I_0$ and $I$ are incident and transmitted intensity of the radiation at a given wavelength. Since transmittance $T=I/I_0$, A=1 corresponds to a case when only 10% of the radiation was transmitted; at A=2 incident radiation is reduced 100 times. Absorbance was measured with a Perkin-Elmer Lambda 35 UV-VIS spectrophotometer. Instrument settings were as follows: 190-1100 nm scan range, 480 nm/min scan speed, 1 nm data interval, 1 sec. cycle time, and 1 nm slit width. Lamp change-over wavelength was set at 326 nm. Liquid samples were measured by placing in 1-cm thick quartz (QS) cells (quartz rectangular cell from Sigma-Aldrich).

Figure 3:
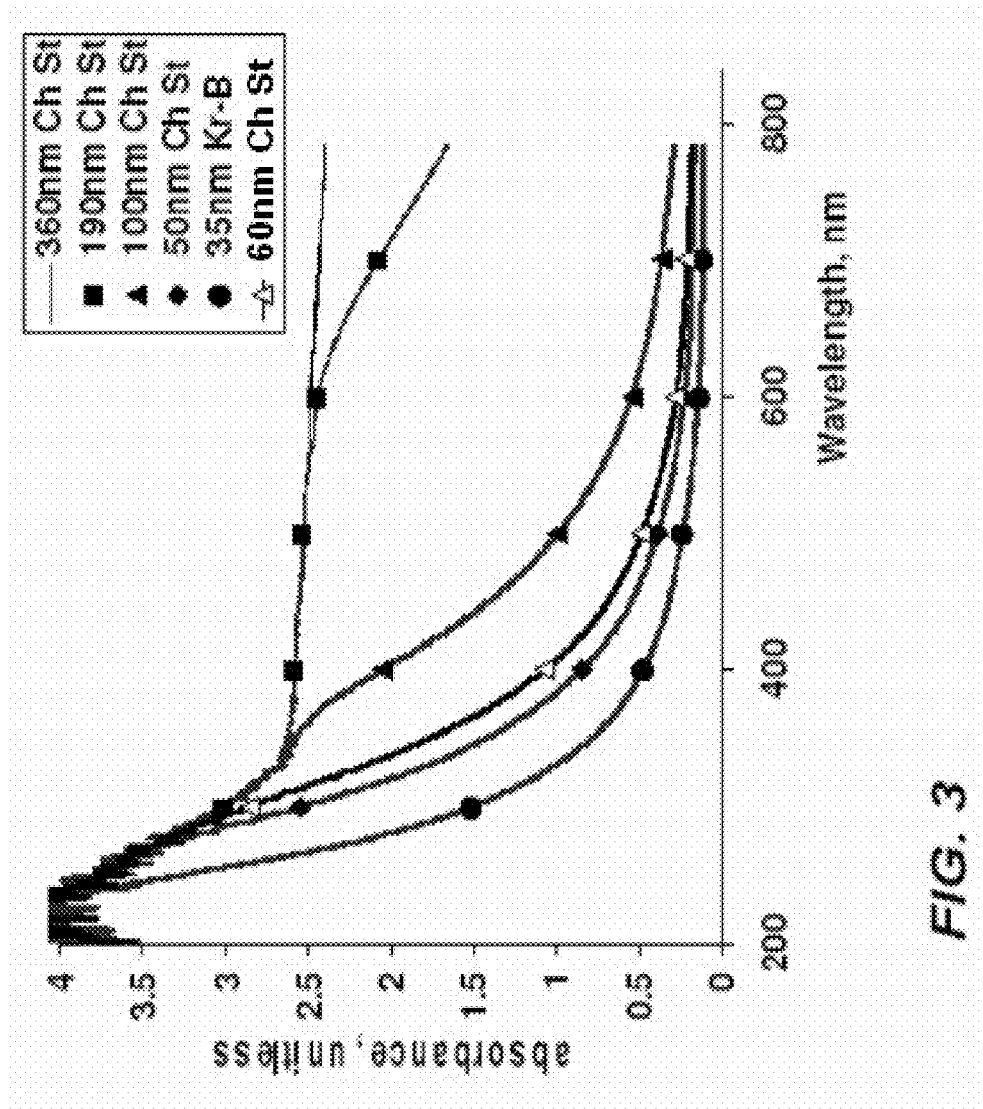
FIG. 3 illustrates UV-VIS absorbance spectra of 0.17 wt % of fractions of different sizes for two types of nanodiamond particles (heat treated Ch St and Kr-b) dispersed in DI water.
Figure 4:
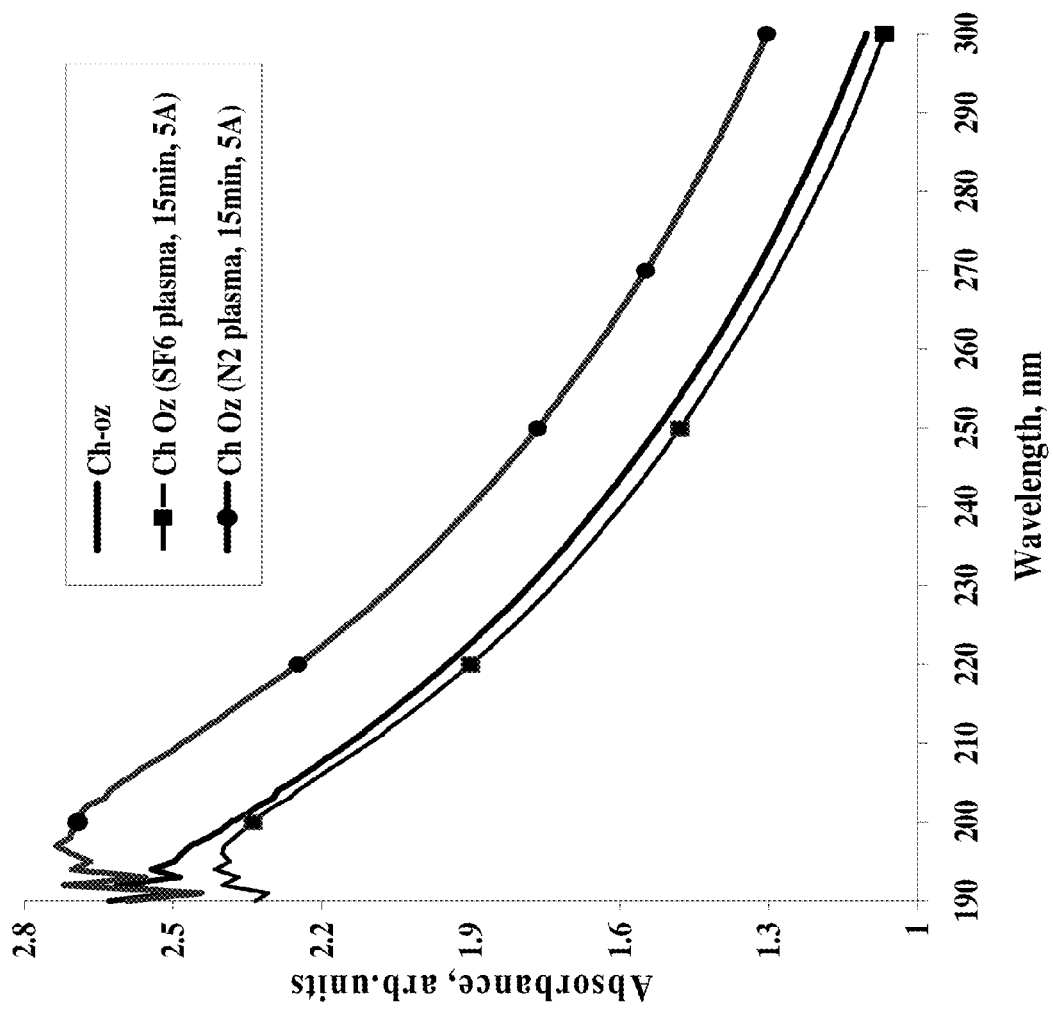
FIG. 4 illustrates UV absorbance spectra of 0.01 wt % of Ch Oz nanodiamond particles dispersed in DI water. Pristine Ch Oz as well as Ch Oz treated in $N_2$ and $SF_6$ plasmas are demonstrated.
Figure 5:
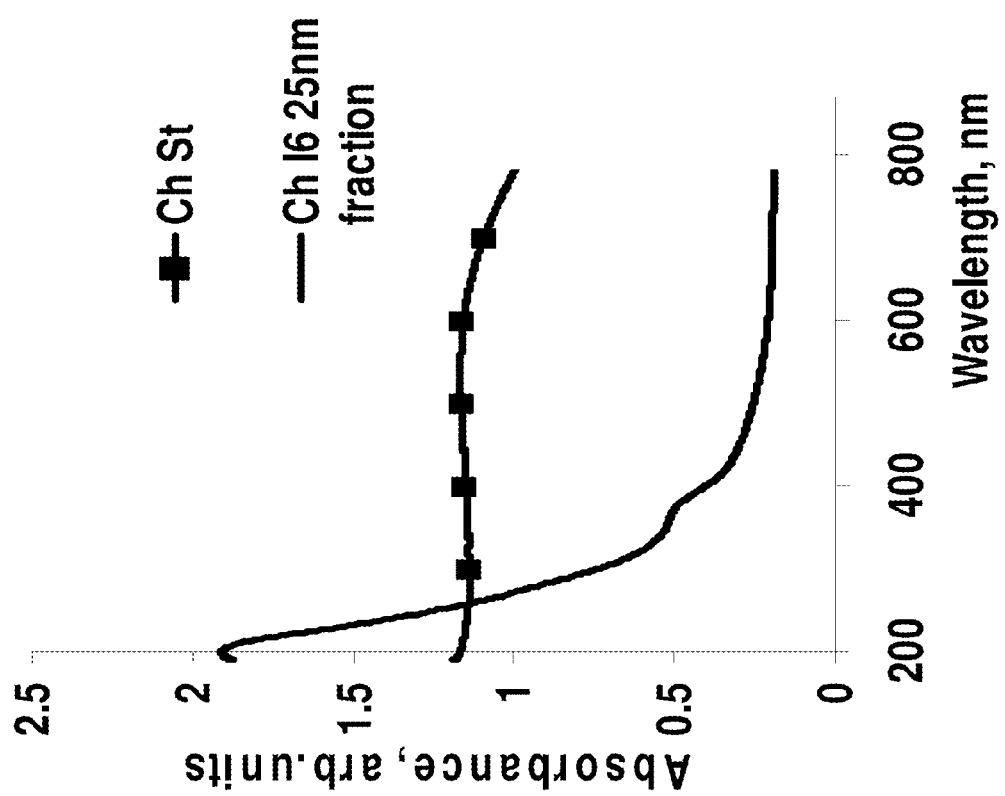
FIG. 5 illustrates UV-VIS absorbance spectra of nanodiamond films obtained by drying of nanodiamond water suspensions on quartz substrates. A film made of Ch-St sample before and after exposure to the sun radiation as well as spectra of dried nanodiamond films for 25 nm average particle size fraction of Ch 16 sample.

In the following examples, the following reference blanks were used: for spectra taken for suspension the reference was always a quartz cell with related solvent without ND (for FIGS. 1-4, and 10). For dried films, reference used was a quartz substrate or cell without nanodiamonds (FIG. 5). For FIG. 6, the reference used was the same amount of silicon grease without ND spread over a quartz cell. For FIGS. 7-8, the reference was a blank quartz cell. For FIG. 9, the reference used was the same amount of lip balm without ND spread over a quartz cell.

Example 1

Four types of DND were used in this experiment; Dol, Ch oz, Ch St and Ch Oz Black. Ch Oz-Black is a fraction of Ch Oz obtained by taking supernatant from a water suspension of Ch-Oz centrifuged at 25,000 G-force for 15 min. Then Ch Oz-black powder was obtained from the supernatant by evaporating the water. DND powders of the four types of ND in the amount of 10 mg/1 ml of DI water were dispersed in 10 ml of DI water. Dol, Ch Oz and Ch St powders were dispersed by mixing at 2,500 min⁻¹ for 2 min using a Fisher Scientific mixer. Ch Oz Black powder was dispersed using sonication. Sonication was carried out using a sonicator equipped with a tapered titanium horn with a tip diameter of 3 mm (Cole-Panner® 750-Watt Ultrasonic Homogenizer EW-04711-60, 20 kHz) that was directly immersed into the sample. The output power was 10 W, output intensity ~100 W/cm². Then the suspension was diluted to the final concentration of 0.1 wt. % of DND. The size of Ch St, Dol, Ch Oz and Ch Oz-black sonicated in water suspensions are 300 nm, 230 nm, 200 nm and 80 nm, correspondingly as recorded by the PCS method.

All samples were tested at the same conditions; the sample volume for absorption measurement was 4 ml. The UV-VIS spectra were recorded using as a reference a quartz cell filled with pure DI water. Pure water does not absorb significantly in the wavelength range 200-900 nm.

The recorded spectra between approximately 200 and 800 nm are illustrated in FIG. 1 (the data for the Dol sample are not shown in order to simplify the figure and make the presentation of the data less crowded). As can be seen from the spectra, all 3 types of DND show high absorbance in the UV region; in addition, the Ch Oz and Ch St samples show high absorbance in the VIS region. The spectrum for the Dol sample (not shown in the FIG. 1) is located between the Ch Oz and Ch St spectra. This is consistent with a fact that polydispersed samples of Ch St, Dol and Ch Oz of 0.1 wt % concentration were not optically transparent when observed with an unaided eye, while it is possible to see through the 0.1 wt. % Ch Oz-Black water suspension.

While not wishing to be constrained by theory, it is believed that in the UV light range, the UV attenuating by the diamond particles is based on their ability to absorb UV light and to scatter it. The efficiency of diamond particles to absorb UV light appears to be dependent on the presence of sp² carbon, intrinsic defects and, to a lesser extent, on the presence of superficial chemical groups that absorb UV light. Efficiency of scattering of UV light by diamond particles depends on particle size, number of particles per unit volume and difference in refractive indexes between particles and dispersive media. Of the four samples tested, it was most difficult to disperse Ch St in water suspension (larger aggregate sizes and lower resistance to sedimentation). It is possible that sedimentation of the particles of the larger sizes decrease content of ND in the sample and resulted in lower UV absorption for the Ct St sample prepared by above conditions.

Again emphasizing that the present invention is not bound by the theory presented, in part, the difference in the UV attenuation between Ch Oz and Ch St samples that can be seen in FIG. 1 can be possibly attributed to the difference in the density of $sp^2$ carbon and the nature of surface groups present (see TABLE 1). The example demonstrates that different types of DND have different UV attenuating properties, but each exhibited such properties. Particularly, water suspensions of polydispersed DND obtained by ozone purification as well as its fraction of a smaller size possess good UV attenuation property (in addition, Ch Oz also possess good visible radiation attenuation). FIG. 1 also illustrates that ND formulations can have different compositions/particle sizes so that it can be transparent or not transparent in the VIS spectrum while absorbing in the UV region. By using a smaller fraction size it is possible to have a sample transparent in the visible wavelength region (FIG. 1).

Example 2

Three types of DND were used in this experiment: Dol, Ch Oz and Ch St. Sample preparation for the UV-VIS spectra is similar to that described in EXAMPLE 1. DND powder, in the amount of 10 mg/1 ml of DI water, was dispersed in DI water using mixing with a shaker. Then the suspension was diluted to the final concentration 0.01 wt. % of DND.

Figure 2:
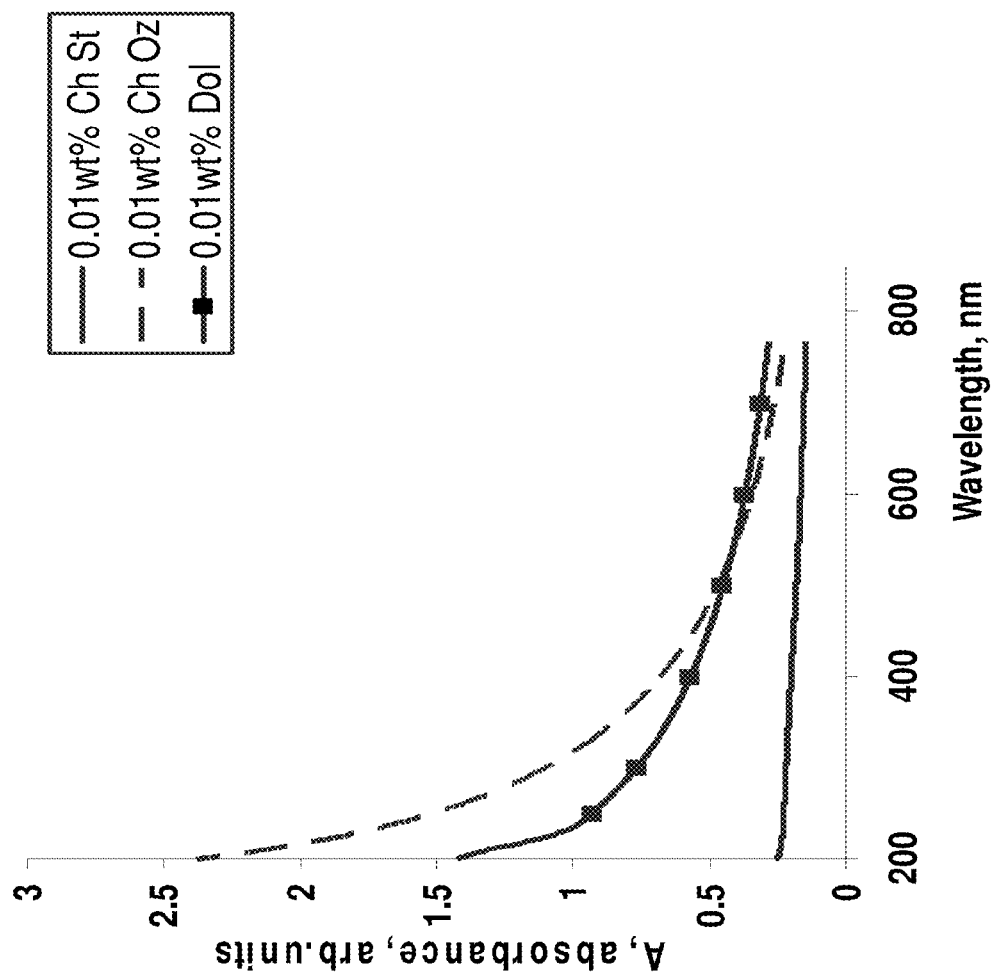
FIG. 2 illustrates UV-VIS absorbance spectra of 0.01 wt % of three types of polydispersed nanodiamond particles (Ch St, Ch Oz and Dol) dispersed in DI water.

FIG. 2 illustrates absorbance spectra between approximately 200 and 800 nm of 0.01 wt. % DND samples produced by different synthesis technique (Dol and Ch-series) and purified by three different methods. Again, Ch Oz sample shows superior UV attenuation at this concentration. This sample contains a high amount of oxygen-containing groups and has the best dispersivity in water out of the three samples. Ch Oz and Dol samples demonstrate quite appreciable absorbance even at 0.01 wt % in water suspension.

Example 3

In this series of experiments Ch St DND and Kr-b were used. The purpose of this experiment was to obtain DND water suspensions of large and small particles sizes at the same concentration for comparison of their UV shielding properties. Ch St was surface—modified in order to improve its dispersivity in water. For this, Ch St powder was placed in an open jar then heated at a rate of 10 degrees/min up to 425° C. in an oven in air and then held at this temperature for 1 hour and cooled within an hour down to room temperature. This helped to obtain powder that disperses well in water, likely due to the increased amount of oxygen-containing groups. Then the sample was dispersed in water and fractionated using a centrifuge to obtain fractions with aggregate sizes of 360 nm, 190 nm, 100 nm, 60 nm and 50 nm. Dried powders of the fractions 360 nm and 190 nm were obtained by evaporating the water. The smallest fractions of Ch St were not dried to avoid possible agglomeration during drying. Their concentrations were measured by evaporating and weighing known volumes of the suspension. By knowing sample concentration, it is easy to dilute it to the target concentration.

The Kr—B sample was also fractionated using the centrifuge to obtain 100 nm, 40 nm and 35 nm aggregate size fractions. It is known that Kr—B fractions do not agglomerate during drying, so, dried powders of the 100 nm, 40 nm and 35 nm fractions of the Kr—B were obtained by evaporating water. The smallest concentration of Ch St suspensions was 0.17 wt. % for 50 nm fractions. All other samples for UV-VIS spectral analysis were prepared at the same target 0.17 wt. % concentration by diluting 100 nm and 60 nm Ch St suspension or dissolving the necessary amount of dried powders of DND fractions in DI water. All suspensions were sonicated for 2 minutes. The sample preparation procedure for UV-VIS spectroscopic analysis is the same as in EXAMPLE 1.

Fractions 360 nm and 190 nm were light- and dark-grey, correspondingly. Suspensions of the fractions 100 nm and below were optically transparent, both 100 nm fractions for Ch St and Kr—B were brownish, 60, 50, 40 and 35 nm fractions showed a transition from light brownish to yellowish colors. The suspensions of the smallest fractions were more transparent. FIG. 3 illustrates the UV-VIS spectra between approximately 200 and 800 nm for selected water suspensions of the fractions. Fractions 360 nm and 190 nm show large absorbance in both the UV and VIS spectra. Fractions 100 nm for both Ch St and Kr—B showed rather similar spectra (the latter was not included in FIG. 3), slightly larger absorbance was observed for the 100 nm Ch-St sample. According to FIG. 3, the most appealing for UV shielding compositions for transparent cosmetic or sunscreen applications would be about 100 nm fractions, which demonstrate very high UV shielding in the range 200-400 nm, while possessing transparency in the VIS range. Larger agglomerates could be used where transparency is not a consideration.

Also, it can be noted that the curve corresponding to 100 nm Ch St sample is similar to the spectrum for 100 nm Kr-b, (not shown in FIG. 3), and a specific absorbance shoulder between 330 nm and 400 nm wavelengths can be observed. This shoulder indicates additional UV absorption in this range. This can be possibly due to Nitrogen defects since all samples contain up to 2.5 wt % of nitrogen. Due to the rapid increase in UV absorbance when particle sizes are increased to 60 nm and above, these particles are believed particularly well suited for UV protection products for both UV-A and UV-B protection. This aspect is discussed further after discussion of all experiments. Note that all samples at all particle size demonstrate very high absorbance in the UV-C region.

Example 4

In this series of experiments the influence of active surface alteration of DND powder on its UV screening capacity was studied. The as-received nanodiamond samples were processed using an atmospheric pressure plasma system (as described in U.S. patent application Ser. No. 11/120,153 filed, May 2, 2005 to Hooke, et al. which is hereby incorporated by reference) that utilizes a dielectric barrier in the generation of the glow discharge. An alumina plate was used as the dielectric barrier placed over the metallic electrodes. The material to be treated was placed between the electrodes using a small tray open at the top to allow exposure to the plasma. ND powder was dehydrated for 2 hrs at 110° C. before plasma treatment. The studies were conducted using $N_2$, $SF_6$, and $CF_4$ as the active gas. Functionalization was carried out by flowing the gases (0.5-5.0 slm) through the system and dissociating the gas in the plasma to produce ions, excited states, and radicals. These species then react with the surface groups of the nanodiamond powder. The duration of treatment varied from 5 to 15 minutes. The pulsed plasma was operated at a repetition frequency of 500 Hz and the current was varied between 2.5 and 10 A. Based on FTIR spectral analysis of several types of the initial ND produced by different vendors, it was demonstrated that plasma treatment of the ND resulted in removal of particular surface groups (such as OH— and C═O, depending on the type of initial ND), as well as in the formation of a variety of carbon-fluorine types of bonding (such as CF, $CF_3(CF_2)$, C═$CF_2$ depending on the surface chemistry of an initial ND).

Powders treated in the plasma were dispersed in water to produce 0.1 wt. % suspensions. Prior to recording the spectrum all samples were thoroughly mixed at 2,500 min$^{-1}$ for 2 min using a Fisher Scientific mixer. When Ch St ND was modified in a $SF_6$ plasma for 5 and 10 min, the treatment resulted in an increase in the optical absorbance in the range 190-215 nm (data not shown). There was no significant difference between the absorption of a sample treated for 5 min with that of a sample treated for 10 min. The increase in optical absorbance following the $SF_6$ plasma treatment could possibly be explained by the surface etching of ND accompanied with the formation of lone electron pairs and unsaturated groups. Similar results were observed with Dol ND modified with a $SF_6$ plasma for 5 and 10 min (data not shown). The opposite effect was observed with the Ch Oz ND. Modification of the Ch-oz with a $SF_6$ plasma gave a slight decrease in optical absorbance in the range 190-300 nm probably because of the reduction in a number of unsaturated bonds (FIG. 4). Interestingly, treatment of Ch Oz ND with a nitrogen plasma resulted in an increase in optical absorbance in the same range (FIG. 4). Since plasma treatment also changed the solubility of powders in water and therefore agglomerate sizes, this also can be a factor for the observed changes in the absorbance spectra.

Example 5

Dried films of DND were prepared on quartz substrates and their absorbance spectra were recorded. In this experiment, 0.8 ml of 1 wt % suspension of polydispersed Ch St ND in water was spread over the 4-cm$^2$ outer wall of a quartz cell and the water was slowly evaporated at room temperature. The resulting amount of DND in the film was 2 mg/cm$^2$. The film was grey and not transparent. In another experiment, a water suspension of 0.5 wt % of a 25 nm fraction of Ch 16 nanodiamond was spread over a 3" quartz wafer (from Silicon West) placed on a hot plate at 120° C. The resulting dry ND film was transparent with a brownish hue. The resulting amount of DND in the film was 1 mg/cm$^2$. FIG. 5 illustrates the absorbance spectra between approximately 200 and 800 nm of the two dried films. The grey non-transparent film prepared from DND suspension with relatively large aggregates using Ch St shows an absorbance that changes slightly over the entire UV-VIS region. Additional spectra for this film were taken after 3-hour afternoon sun exposure in North Carolina during the summer. The two spectra were identical indicating that there was no degradation of the UV protective properties over the three hours of exposure, and thus should provide long lasting protection against UV radiation in sunscreen formulations and cosmetic formulations having sunscreen properties.

Despite the fact that the film made from 25 nm aggregate sizes of ND is very thin and transparent in the VIS region, absorbance in UVA and, especially UVB and UVC is high (FIG. 5). Also, it can be noted from the figure that the specific absorbance shoulder at 340-420 nm wavelength for Ch I6 25 nm fraction (FIG. 5), that improves UV absorption in this range is present. This can be possibly due to the nitrogen defects. Thus thin ND film can be applied by different means for UV protection over different surfaces (skin, mucus membranes, eye, hairs, etc).

Example 6

In this series of experiments absorbance of different types of ND, OLC (onion-like carbon) and TiO2 nanoparticles versus wavelength from a wavelength of 200 to 400 nm was measured for nanoparticles at a concentration of 1-2 mg/cm$^2$ in silicone grease dispersed manually over a quartz substrate. Two types of OLC particles were used—both obtained by annealing of Ch St DND at 1800K and 1900K in vacuum conditions ($5*10^{-4}$-$1*10^{-4}$ torr). TiO2 nanoparticles were obtained from Fisher. Silicone grease is transparent in the UV-VIS region. For sample preparation, 4 mg (for concentration of 1 mg/cm$^2$), 6 mg (for concentration of 1.5 mg/cm$^2$) and 8 mg (for 2 mg/cm$^2$) of nanoparticles was manually mixed with 50 mg of silicone grease and spread over the 4-cm$^2$ outer wall of a quartz cell. The maximum amount of the nanoparticles 2 mg/cm$^2$ spread over a quartz substrates in the examples below was chosen based on U.S. Food and Drug Administration (FDA) recommendations for the amount of sunscreen to be used.

Figure 6:
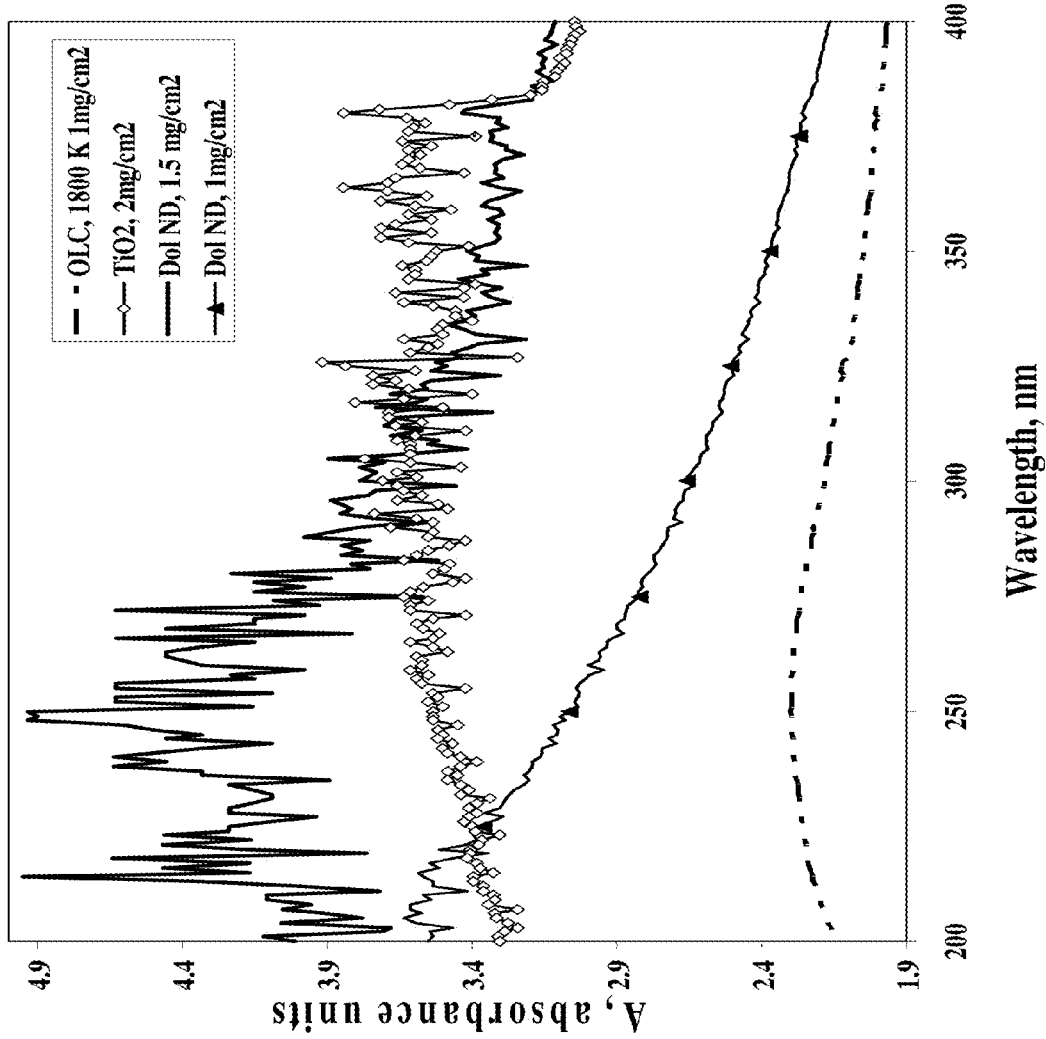
FIG. 6 illustrates the relative absorbance of nanodiamond, OLC and $TiO_2$ nanoparticles dispersed in silicone grease, the silicon grease being transparent in UV-VIS region.

FIG. 6 illustrates the relative absorbance on ND, OLC and $TiO_2$ nanoparticles dispersed in silicone grease. It can be seen that particular ND formulations are comparable to or more efficient at UV attenuation (especially in UVB region) than $TiO_2$ formulations even at a higher concentration (⅓ higher concentration) of $TiO_2$ nanoparticles. Absorbance of OLC annealed at 1900K at an amount of 1 mg/cm2 was about 1.2 for the 200-400 nm wavelength region (not shown in the figure). Note that ND when dispersed in other media (FIG. 6) screens in the UV-VIS region of the spectrum much better than in the form of a dried film (FIG. 5) at similar or even lower concentrations of ND per cm$^2$.

Example 7

Figure 7:
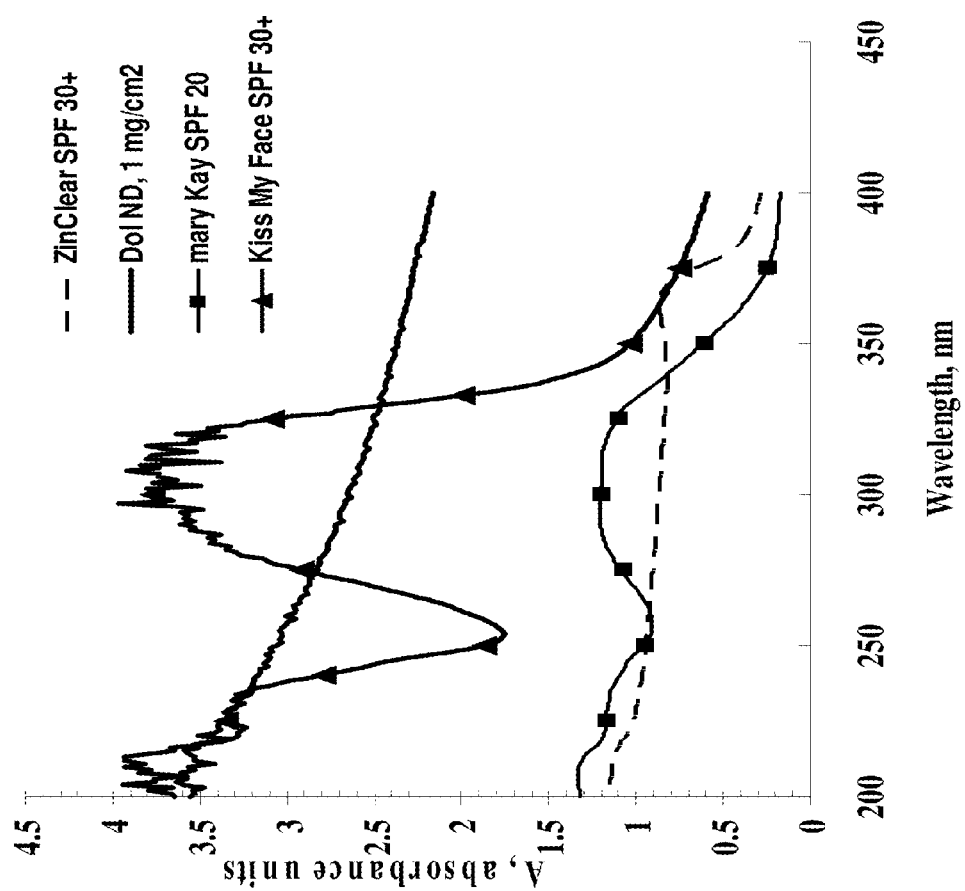
FIG. 7 illustrates the relative absorbance of dispersion of nanodiamond in silicone grease (prepared manually) and sunscreens with SPF 30 and SPF 20 spread over quartz substrates.

In this example the absorbance of DND dispersed in silicone grease is compared with the absorbance of commercial sunscreens. The following commercial sunscreens were used: sunscreen ZinClear™ SPF 30+ by Advanced Nanotechnology Limited, Welshpool, Australia (2 mg/cm$^2$, 15.5% nano ZnO); Sunscreen Mary Kay™, SPF 20 at 2 mg/cm$^2$; Sunscreen Kiss My Face™, SPF 30+ at 2 mg/cm$^2$. Nanodiamond powder Dol was manually dispersed in silicone grease at 1 mg/cm$^2$ (silicone grease plus ND is 13.5 mg/cm2 out of which 1 mg/cm$^2$ is ND). Since silicone grease is very viscose, it required this minimum amount of grease to get the ND relatively uniformly dispersed. FIG. 7 is a graph of the absorbance versus wavelength from a wavelength of 200 to 400 nm of the above samples.

FIG. 7 illustrates that a suspension of ND in silicone grease (prepared manually) at a concentration of ND 1 mg/cm$^2$ is comparable in UV protection with sunscreens with SPF 30 and exceeds those for sunscreens with SPF 20. Based upon these curves, the silicone grease preparation appears to provide better UV protection than the ZinClear™ SPF 30+ containing high concentration (15.5 wt. %) of nano ZnO. The amount of the sunscreen 2 mg/cm$^2$ spread over a quartz substrates in the examples above and below was chosen based on U.S. Food and Drug Administration (FDA) recommendations for measurement of SPF.

Example 8

In this example nanodiamond powder Dol was added to a commercial sunscreen with low SPF. Banana Boat™ brand tanning lotion SPF 4 was used in this example. Formulations of 1 and 2 wt. % of ND-Dol in the SPF4 lotion were dispersed using magnetic stirring (stirred for 20 min, and 1.5 hrs respectively for the two concentrations of ND in formulations of ND-SPF4). The formulations were dispersed over a quartz substrate at an amount of 2 mg/cm$^2$ that results in 0.04 mg/cm$^2$ of ND for the ND-SPF4 lotion formulation with 2 wt. % of ND.

Figure 8:
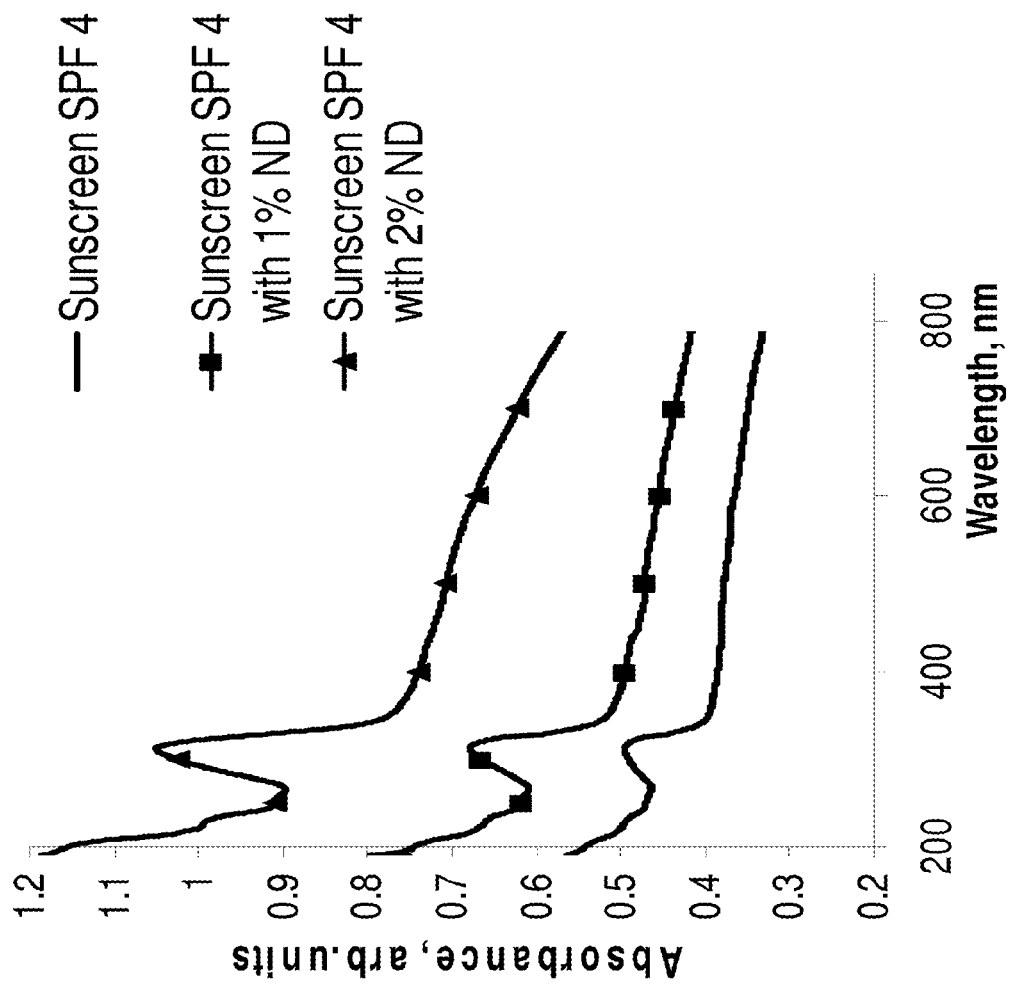
FIG. 8 illustrates the relative absorbance of suspension of different concentrations of nanodiamond in a sunscreen with SPF4 and pure sunscreen.

FIG. 8 illustrates the absorbance versus wavelength between approximately 200 and 800 nm of Banana Boat™ brand tanning lotion SPF 4 and formulations of 1 and 2 wt. % of ND-Dol in the SPF4 lotion and further illustrates how very small additions of ND-Dol nanodiamond powder to a sunscreen formulation improves its performance. The addition of 0.04 mg/cm$^2$ of ND-Dol to ND-SPF4 (resulting in 2 wt. % of ND in the formulation) improved its absorbance from 0.5 to 1.07 adsorption units (3.7 times) and makes SPF4 lotion perform similar to the SPF15-SPF20 lotion. These types of experiments were performed using commercially available sunscreen lotion for the formulations and demonstrated that amounts as small as 1-2 wt. % of well dispersed ND can provide substantial beneficial effect. With reference to the graphical data, use of 1 wt. % addition of ND to the existing sunscreen formulation increased the absorption of UV light at most frequencies by approximately ⅓, while use of 2 wt. % addition of ND to the existing formulation increased the absorption of UV light at most frequencies by approximately a factor of 2, for this particular carrier.

Example 9

In this example dispersivity and resistance to sedimentation of ND-based suspensions in cosmetic formulations were studied. The water-based formulation of L'Oreal (Paris) Pinch of Colour for Lips & Cheeks Blushing™ cosmetic was used as an example. The sample of the original product was diluted 12-times in DI water, but it still preserved a strong red color. Powder of Ch 16 ND which is typically well dispersed in water was dispersed in the diluted product formulation in the amount of 0.1 wt. % using mixing. The ND sedimented from the suspension within minutes. In another experiment, 3 ml of the 0.2 wt % water suspension of the 40 nm fraction of Ch 16 was added to 3 ml of the 12-times diluted product and mixed. It appeared that the ND did not sediment in this preparation; the sample remained visibly transparent and exhibited a slightly violet hue as compared to the sample prepared from 3 ml of 12-times diluted product with addition of 3 ml pure water (so that only difference between the samples was the addition of ND to one of them). The new hue was considered appealing to the eye.

Example 10

In this experiment, Mary Kay™ Satin Lips™ brand Lip Balm was used. Dispersion of the powder of dried 25 nm fraction of St 16 nanodiamond in the lip balm was prepared. For sample preparation, 8 mg of nanoparticles were manually mixed with 25 mg of lip balm and spread over the 4-cm$^2$ outer wall of a quartz cell. This resulted in 2 mg of ND per cm$^2$ of the substrate. A control sample containing 20 mg of Lip Balm spread over the 4-cm$^2$ outer wall of a quartz cell was prepared for comparison. The absorbance spectra were taken for the lip balm with and without ND.

Figure 9:
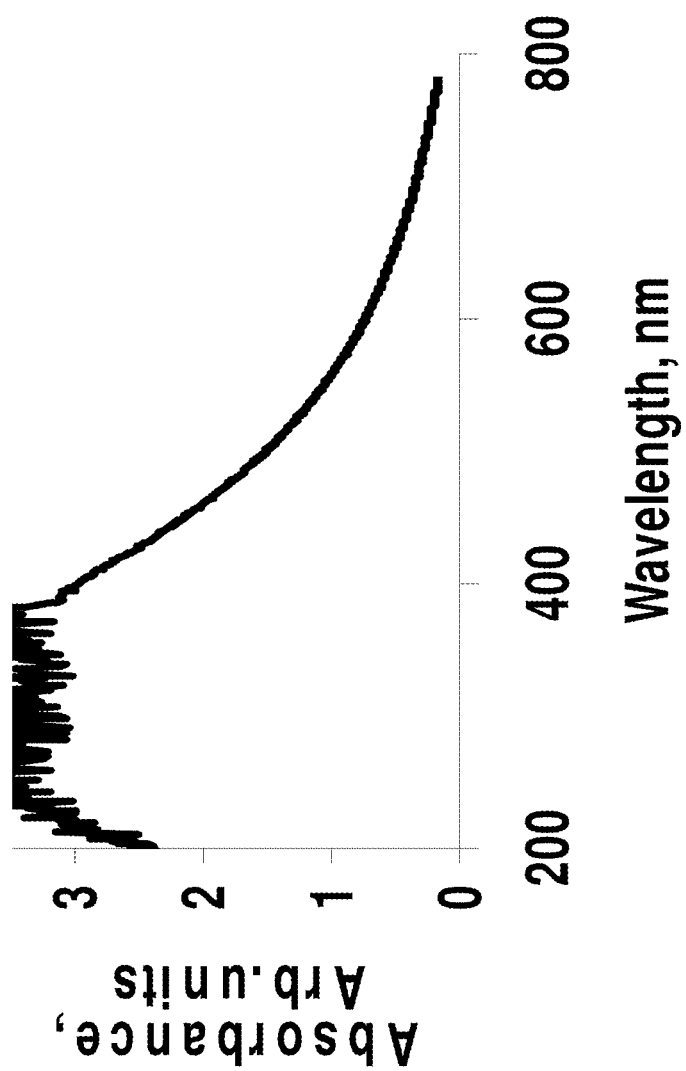
FIG. 9 illustrates the relative absorbance of a dispersion of dried 25 nm fraction of Ch 16 nanodiamond in Mary Kay Satin Lips™ brand Lip Balm (prepared manually) versus pure Mary Kay Satin Lips™ brand Lip Balm spread over quartz substrates.

FIG. 9 illustrates the relative absorbance the sample containing ND dispersed in the Lip Balm versus a sample with pure Lip Balm. It can be seen that ND formulation is efficient in UV screening.

Example 11

Nanodiamond films formed by drying 25 nm Ch St 16 ND suspensions on quartz substrates as described in EXAMPLE 5 were used in this series of experiments. The ND films confined between 2 quartz substrates were visually transparent with a brownish hue. This ND coated quartz structure was placed over several samples which otherwise lost their color quickly under sun exposure in July in North Carolina. As samples to demonstrate the protection from sun exposure provided by ND films, pink post-it page markers (3M (670-5AF)) were used. The page marker was covered in a way that part of it was covered by quartz coated with a ND film, part was covered with only pure quartz and part was open to air. After 2-days of sun exposure, there was a visible boundary between the more bright pink color preserved under the ND film and the faded color of the marker that was not protected with ND film. This example provides basic evidence of attenuation of UV light transmission by the ND particles, providing confirmation of the more sophisticated spectrometer measurements.

Example 12

Figure 10:
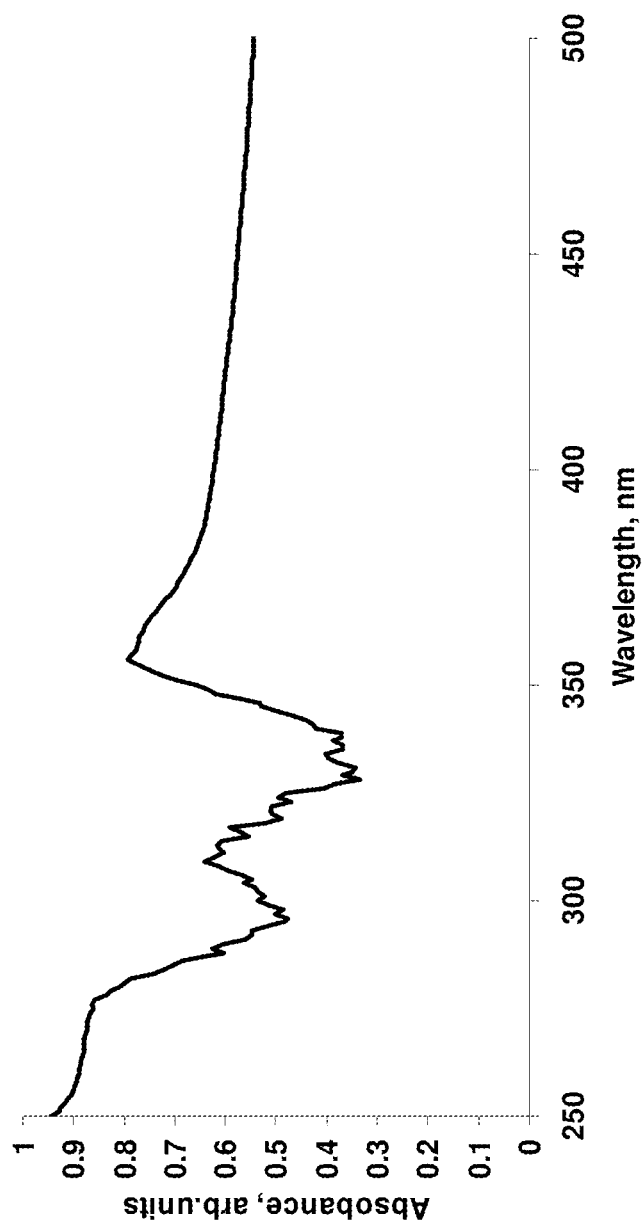
FIG. 10 illustrates the relative UV-VIS absorbance of a Galyfilcon™ A contact lens immersed for 30 min to 0.6 wt % water suspension of 60 nm fraction of Ch 16 ND versus an untreated lens.

In this example treatment of a contact lens with ND particle additions are shown to provide better protection from harmful UV light. A Galyfilcon™ brand Contact lens produced by Johnson&Jonhson was immersed in a 0.6 wt % water suspension of ND. The ND was the 60 nm particle size fraction of Ch I6. The lens was left in a suspension for 30 minutes, so that ND particles can adhere to the lens surface and possibly soak into the film. There was no visible difference in the appearance of the lens after this procedure. Then UV-VIS spectra were taken for sample of a pristine contact lens and for the lens soaked in ND suspension. FIG. 10 illustrates the relative spectra of the lens with ND as compared to a baseline spectra of the pristine lens (i.e., the difference between the two spectra is depicted in FIG. 10). An increase in UV-VIS absorption can be seen in the figure due to nanodiamonds.

TABLE 1

FTIR analysis of the surface composition of the ND used in the present study.

| Chemical group | Ch St | Ch I6 | Ch Oz (same Ch Oz-Black) | Kr-b | Dol |
|---|---|---|---|---|---|
| O—H free, O—H, H bridge (OH) | 3573 cm$^{-1}$ weak | Shoulder 3590 cm$^{-1}$ | 3596 sh | 3588 sh | — |
| —NH$_2$, =NH, >NH | 3432 cm$^{-1}$ broad | 3432 cm$^{-1}$ broad | 3423 | 3410 | 3423 |
| Above and -—CONH— —CONH$_2$— | — | — | — | 3245 sh | 3250 sh |
| Methyl asym | 2960 cm$^{-1}$ very weak | — | 2960.1 | — | 2972.2 |
| Methylene asym | 2930 cm$^{-1}$ weak | — | 2931 | 2927.9 | 2927.9 |
| Methylene sym | 2858 cm$^{-1}$ very weak | — | 2859.5 | 2851.9 | 2855.5 |

TABLE 1-continued

FTIR analysis of the surface composition of the ND used in the present study.

| Chemical group | Ch St | Ch I6 | Ch Oz (same Ch Oz-Black) | Kr-b | Dol |
|---|---|---|---|---|---|
| R—C(=O)—O—C(=O)—R Satur | — | 1799 cm$^{-1}$ as well at 1289 cm$^{-1}$ | 1813.1 | 1773.9 | — |
| R—C(=O)—O—C(=O)—R unsatur | 1725 cm$^{-1}$ | — | — | — | 1732.6 |
| —NH$_2$, >C=C< | 1631.6 cm$^{-1}$ | 1631.6 cm$^{-1}$ | 1628.0 | 1627.3 | 1632.0 |
| R—C(=O)O— | — | — | — | — | 1551.5 |
| H1a diamond feature, N-related (possibility) | — | Very weak shoulder 1460 cm$^{-1}$ | — | — | — |
| CH in CH$_3$, CH$_2$ | — | — | 1446.1 | 1448.4 | — |
| —CH$_3$, >C(CH$_3$)$_2$ | — | — | 1370.1 | — | 1385.4 |
| >N—NO$_2$ | — | — | 1275.2 | 1319.6 sh | — |
| C—N=O | — | — | 1225.9 | 1210.5 | 1267.2 |
| C—OH, adsorbed CO, CO$_2$ | 1120.2 cm$^{-1}$ medium | — | 1060.1 | — | — |
| >C=C(H)— | 802 cm$^{-1}$ extremely weak | — | — | 920.74 | — |
| 3 neighboring aromatic C—H | 781 cm$^{-1}$ extremely weak | — | — | — | — |
| C—H | 620 cm$^{-1}$ weak | — | 593.6 | 593.6 | 581.1 |

Figure 11:
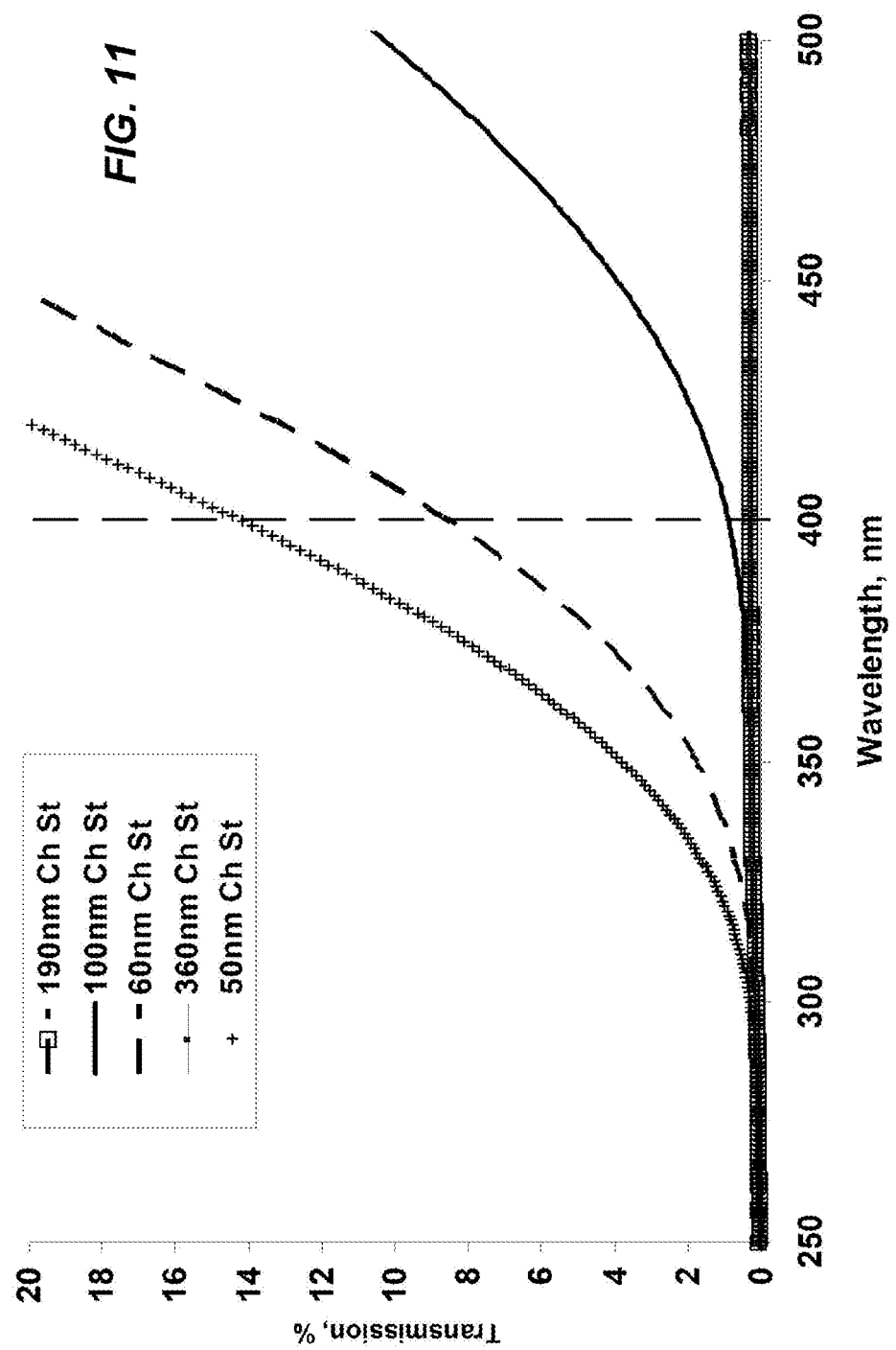
FIG. 11 illustrates light transmission for various agglomerate sizes over the ultraviolet spectrum (and beyond) and is analogous to FIG. 3 except expressed in percent transmission.

FIGS. 11-12 depict similar information as that shown in FIG. 3 from the experiments of EXAMPLE 3. This graph was reconstructed to display transparency to UV radiation (rather than absorbance), and to compress the scale to more readily see the dramatic change in UV absorption exhibited near the 400 nm range as a function of particle size. In the case of FIG. 12, the performance at 350 and 400 nm are directly compared by representing these wavelengths as curves. As a result of this experiment, it can be concluded that use of initial particle agglomerate sizes in the range of 60 to 150 nm can be used to substantially increase the UV attenuation without significant impact on visible transparency in relatively low concentrations of ND particles. When the visual presence of the particles is of secondary consideration, or used to augment pigmentation, even larger size particle agglomerates can be used to produce even greater UV absorption. It is noted that the particle agglomerate sizes may increase to varying degrees in formulating the cosmetic product dispersion. This factor should be taken into consideration when determining how to formulate a UV protecting sunscreen or cosmetic based upon the desired protection and visibility of the resulting product when in use. At this scale, the 190 and 360 nm particle agglomerate performance is too high to be readable on the graph, but is nonetheless shown for completeness.

In accordance with certain embodiments, cosmetic preparations can be formulated by disbursing nanodiamond particle agglomerates with sizes of 60 to 150 nm if the formulation is to have minimal visible impact as a result of the nanodiamonds (assuming that the formulation process does not cause additional agglomeration above about 150 nm. Particle agglomerates larger than 150 nm can be used if the visible impact is not important or secondary or used in the pigmentation process. Cosmetic formulations that can be devised to incorporate such ND agglomerates include, but are not limited to sunscreens, creams, foundations, concealers, powders, blushes, body sprays, body sticks, paints and tattoos, hair colors, gels and sprays, coatings, glosses, overlays and, lipsticks, lip gloss, mascara, eyeliner, eye shadow, and other human and animal compatible compositions. Such formulations are currently believed compatible with almost any cosmetically suitable base material.

Thus, in accordance with certain embodiments consistent with the present invention, a cosmetic or sunscreen preparation that provides transmission attenuation of at least a portion of ultraviolet A, B and C radiation with wavelengths between approximately 190 and 400 nm when applied to human tissue thereby reducing the human tissue's exposure to the ultraviolet radiation, is made up of a dispersion of an effective amount of diamond nanoparticles in a physiologically compatible medium, where at least a portion of the diamond nanoparticles have a size greater than about 60 nm, so that the diamond particles provide ultraviolet light transmission attenuating properties in the dispersion.

Similarly, a method of manufacturing a cosmetic or sunscreen preparation that provides attenuation of at least a portion of ultraviolet A and B and C radiation having wavelengths between approximately 190 and 400 nm involves providing a pharmacologically suitable medium; providing diamond nanoparticles having a size greater than about 60 nm; and blending the nanodiamond particles into the pharmacologically suitable medium to produce a dispersion, wherein the diamond nanoparticles provide ultraviolet light transmission attenuation properties to the dispersion.

In certain embodiments, at least a portion of the diamond nanoparticles have a size of approximately 60-150 nm, and in certain embodiments at least a portion of the diamond nanoparticles have a size of approximately 100 nm. In certain embodiments, the diamond nanoparticle make up between about 0.1 and 10.0 percent by weight of the preparation, and in certain embodiments the diamond nanoparticles make up between about 0.5 and 5.0 percent by weight of the preparation. In other embodiments, the diamond nanoparticles make up between about 1 and 5 percent by weight of the preparation, and at least a portion of the diamond nanoparticles have a size of approximately 60 to 150 nm. In certain other embodiments, the diamond nanoparticles comprise greater than 1 percent by weight of the preparation and at least a portion of the diamond nanoparticles have a size of approximately 100 nm. In certain embodiments, the diamond nanoparticles agglomerates can have an average size of approximately 60-150 nm.

In certain embodiments, the nanoparticle concentration is less than a concentration that is visible to the unaided eye when applied to human tissue. In certain embodiments, the dispersion is carried out in a manner that as to cause the diamond nanoparticles to agglomerate to sizes less than about one micron. In certain embodiments, the medium is a cosmetic medium can be selected from a cream, a lotion, a lipstick, a lip balm, a lip gloss, a makeup foundation, a makeup skin tinting preparation, a concealer, a powder, an oil, a sprayable liquid, a gel, a wax and an emulsion. The medium can be a sunscreen medium that is selected from a skin cream, a skin lotion, a gel, and a sprayable liquid. The preparation may also incorporate another type of ultraviolet inhibitor, such as for example, titanium dioxide, zinc oxide, or organic ultraviolet inhibitors.

In certain embodiments, the cosmetic or sunscreen preparation's diamond particles can be modified as a result of wet or gas phase chemical reaction(s), or chemical reactions induced photochemically, electrochemically, mechanochemically, or by means of a plasma, irradiation or sonic energy to obtain ND particles with an enhanced ability to absorb UV radiation. In certain embodiments, the diamond particles increase the UV radiation attenuation of the preparation by at least 33% across the UV frequency spectrum.

An exemplary sunscreen preparation that attenuates transmission of at least a portion of ultraviolet A, B and C radiation with wavelengths between approximately 190 and 400 nm when applied to human tissue to thereby reduce the human tissue's exposure to the ultraviolet light consistent with certain embodiments is made up of a dispersion of an effective amount of diamond nanoparticle agglomerates, where at least a portion of the diamond nanoparticles have a size between about 60 and 300 nm, and wherein the concentration of the diamond nanoparticle agglomerates comprise between about 0.1 and 10 percent by weight, so that the diamond particles provide attenuation of transmission of the ultraviolet light in the dispersion.

While certain illustrative embodiments have been described, it is evident that many alternatives, modifications, permutations and variations will become apparent to those skilled in the art in light of the foregoing description.

What is claimed is:

1. An ultraviolet light attenuating preparation, comprising:
a dispersion of an effective amount of diamond nanoparticles in a physiologically compatible medium, where a plurality of the diamond nanoparticle comprise a size greater than about 60 nm and less than about one micron;
where the diamond nanoparticles provide ultraviolet radiation transmission attenuating properties for ultraviolet radiation having a wavelength between approximately 190 and 400 nm; and
where at least a portion of the diamond nanoparticles comprise modified diamond nanoparticles that are modified to exhibit internal defects or color centers within the diamond nanoparticles.

2. The preparation according to claim 1, where at least a portion of the diamond nanoparticles comprise electron irradiated diamond nanoparticles.

3. The preparation according to claim 2, where the electron irradiated diamond nanoparticles comprise annealed diamond nanoparticles.

4. The preparation according to claim 1, where the diamond nanoparticles comprise diamond nanoparticles modified by oxidation.

5. The preparation according to claim 4, where the diamond nanoparticles modified by oxidation are modified by exposure to acids, oxygen or ozone.

6. The preparation according to claim 1, where at least a portion of the diamond nanoparticles comprise ion irradiated diamond.

7. The preparation according to claim 6, where the ion irradiated diamond nanoparticles comprise annealed diamond nanoparticles.

8. The preparation according to claim 1, where at least a portion of the diamond nanoparticles comprise modified diamond nanoparticles that are modified by:
at least one of wet or gas phase chemical reaction, or chemical reactions induced photochemically, electrochemically, mechanochemically, or exposure to a plasma, or exposure to sonic energy, or by oxidation with acids, oxygen or ozone or exposure to irradiation, or annealing.

9. The preparation according to claim 1, where at least a portion of the diamond nanoparticles are modified by at least one of:
irradiating the diamond nanoparticles;
annealing the irradiated diamond nanoparticles; and
oxidization of the diamond nanoparticles.

10. The preparation according to claim 1, where the modified diamond nanoparticles are modified by irradiation and then annealed.

11. The preparation according to claim 1, where the modified diamond nanoparticles are modified to enhance absorption or photoluminescence when exposed to light due to increased structural defects comprising N—V centers, defect centers due to dopant atoms, self-interstitials, vacancies, complexes of the above, complexes of charged defects, or dislocations that cause absorption.

12. The preparation according to claim 1, wherein the diamond nanoparticles are produced by detonation, shock wave, or chemical vapor deposition, or homogeneous nucleation of diamond powder in the gas phase, or obtained by processing of micron-sized diamond particles of high-pressure-high-temperature diamond synthesis; or where the diamond nanoparticles comprise naturally occurring diamond particles.

13. The preparation according to claim 1, where the diamond nanoparticles comprise functionalized diamond particles or diamond particles with attached organic molecules.

14. The preparation according to claim 1, where the modified diamond nanoparticles comprise diamond nanoparticles having a functionalized surface that enhances absorption of ultraviolet radiation compared to their unmodified state.

15. The preparation according to claim 1, where the modified diamond nanoparticles comprise diamond nanoparticles having surface functionalization to enhance stability in a carrier or liquid, or provide chemical compatibility with the physiologically compatible medium compared to their unmodified state.

16. The preparation according to claim 1, where the modified diamond nanoparticles comprise diamond nanoparticles having surface functionalization to enhance resistivity to agglomeration and sedimentation compared to their unmodified state.

17. The preparation according to claim 1, where the modified diamond nanoparticles comprise diamond nanoparticles having attached organic molecules that enhance absorption of ultraviolet radiation compared to their unmodified state or comprise a composition in combination with other sunscreen agents that can be chosen from organic screening agents, inorganic physical screening agents and their mixtures.

18. The preparation according to claim 1, where a plurality of the diamond nanoparticles have color centers induced by doping.

19. The preparation according to claim 1, where the modified diamond nanoparticles comprise irradiated diamond nanoparticles.

20. The preparation according to claim 1, where at least a portion of the diamond nanoparticles comprise gamma-ray irradiated diamond nanoparticles.

21. The preparation according to claim 20, where the gamma-ray irradiated diamond nanoparticles are modified by annealing subsequent to irradiation.

22. The preparation according to claim 1, where the diamond nanoparticles further exhibit radiation transmission attenuating properties for ultraviolet radiation having a wavelength between approximately 190 and 300 nm.

23. The preparation according to claim 1, where the diamond nanoparticles comprise functionalized diamond nanoparticles, and where the functionalized diamond nanoparticles are functionalized with at least one of the materials selected from the group consisting of carboxyl, hydroxyl, amino, carbonyl groups and surface fluoride.

24. An ultraviolet light attenuating preparation, comprising:
a dispersion of an effective amount of diamond nanoparticles in a physiologically compatible medium, where a plurality of the diamond nanoparticle comprise a size greater than about 60 nm and less than about one micron;
where the diamond nanoparticles provide ultraviolet radiation transmission attenuating properties for ultraviolet radiation having a wavelength between approximately 190 and 400 nm;
where at least a portion of the diamond nanoparticles comprise:
first modified diamond nanoparticles that are modified by doping to create color centers; and
second modified diamond nanoparticles that are modified to exhibit enhanced photoluminescence and enhanced absorption of ultraviolet radiation compared to unmodified diamond nanoparticles, where the second modified diamond nanoparticles comprise diamond nanoparticles that are modified by:
electron, ion or gamma-ray irradiation of the diamond nanoparticles; and
annealing of the irradiated diamond nanoparticles.

25. An ultraviolet light attenuating preparation, comprising:
a dispersion of an effective amount of diamond nanoparticles in a physiologically compatible medium, where a plurality of the diamond nanoparticle comprise a size greater than about 5 nm and less than about one micron;
where the diamond nanoparticles provide ultraviolet radiation transmission attenuating properties for ultraviolet radiation having a wavelength between approximately 190 and 400 nm; and
where at least a portion of the diamond nanoparticles comprise modified diamond nanoparticles that are modified to exhibit internal defects or color centers within the diamond nanoparticles.

26. The preparation according to claim 25, where at least a portion of the diamond nanoparticles comprise diamond nanoparticles having size greater than about 25 nm.

27. The preparation according to claim 25, further comprising additional diamond nanoparticles having size within the range from 1 nanometer to 1000 nanometers.

28. The preparation according to claim 1, further comprising a sunscreen agent selected from the group consisting of organic screening agent, inorganic physical screening agent and mixtures of organic and inorganic screening agents.

29. The preparation according to claim 1, further comprising one or more material selected from the group consisting of lotion, cream, moisturizer, absorbent, abrasive, anticaking agent, antifoaming agent, antioxidant, binder, biological additive, buffering agent, bulking agent, chelating agent, colorant, cosmetic astringent, cosmetic biocide, denaturant, drug astringent, external analgesic, film former, fragrance component, pH modifier, plasticizer, preservative, propellant, reducing agent, skin bleaching agent, emollient, humectant, occlusive agent, skin protectant, solvent, foam booster, hydrotrope, solubilizing agent, suspending agent, sunscreen agent, ultraviolet light absorber, waterproofing agent, viscosity increasing agent, emollient, humectant, dry-feel modifier, waterproofing agent, insect repellant, sunless artificial tanning agent, vitamin, chelating agent and fragrance.

30. An ultraviolet light attenuating preparation, comprising:
a dispersion of an effective amount of diamond nanoparticles in a physiologically compatible medium, where a plurality of the diamond nanoparticle comprise a size greater than about 60 nm and less than about one micron;
where the diamond nanoparticles provide ultraviolet radiation transmission attenuating properties for UVC radiation; and
where at least a portion of the diamond nanoparticles comprise modified diamond nanoparticles that are modified to exhibit internal defects or color centers within the diamond nanoparticles.

31. An ultraviolet light attenuating preparation, comprising:
a dispersion of an effective amount of diamond nanoparticles in a physiologically compatible medium, where a plurality of the diamond nanoparticle comprise a size greater than about 60 nm and less than about one micron;
where the diamond nanoparticles provide radiation transmission attenuating properties for radiation having a wavelength between approximately 190 and 800 nm; and
where at least a portion of the diamond nanoparticles comprise modified diamond nanoparticles that are modified to exhibit internal defects or color centers within the diamond nanoparticles.

32. The preparation according to claim 31, where the amount of diamond nanoparticles comprises between 0.01 wt % and 10.0 wt %.

33. The preparation according to claim 1, where the amount of diamond nanoparticles comprises between 0.01 wt % and 10.0 wt %.

34. The preparation according to claim 24, where the amount of diamond nanoparticles comprises between 0.01 wt % and 10.0 wt %.

35. The preparation according to claim 25, where the amount of diamond nanoparticles comprises between 0.01 wt % and 10.0 wt %.

36. The preparation according to claim 30, where the amount of diamond nanoparticles comprises between 0.01 wt % and 10.0 wt %.

37. The preparation according to claim 25, where at least a portion of the diamond nanoparticles comprise modified diamond nanoparticles that are modified by:
at least one of wet or gas phase chemical reaction, or chemical reactions induced photochemically, electrochemically, mechanochemically, or exposure to a plasma, or exposure to sonic energy, or by oxidation with acids, oxygen or ozone or exposure to irradiation, or annealing.

38. The preparation according to claim 25, where the modified diamond nanoparticles are modified to enhance absorption or photoluminescence when exposed to light due to increased structural defects comprising N—V centers, defect centers due to dopant atoms, self-interstitials, vacancies, complexes of the above, complexes of charged defects, or dislocations that cause absorption.

39. The preparation according to claim 25, where the modified diamond nanoparticles comprise diamond nanoparticles having surface functionalization to enhance resistivity to agglomeration and sedimentation compared to their unmodified state.

40. The preparation according to claim 25, where the diamond nanoparticles comprise functionalized diamond nanoparticles, and where the functionalized diamond nanoparticles are functionalized with at least one of the materials selected from the group consisting of carboxyl, hydroxyl, amino, carbonyl groups and surface fluoride.

\* \* \* \* \*